(12) United States Patent
Heinegard et al.

(10) Patent No.: US 8,158,577 B2
(45) Date of Patent: Apr. 17, 2012

(54) MODULATION OF CARTILAGE HOMEOSTASIS BY ACTIVE DOMAINS OF CELL BINDING EXTRACELLULAR MATRIX MOLECULES

(76) Inventors: Dick Heinegard, Lund (SE); Lisbet Agneta Camper, Bjared (SE)

( * ) Notice: Subject to any disclaimer, the term of this patent is extended or adjusted under 35 U.S.C. 154(b) by 126 days.

(21) Appl. No.: 12/381,211

(22) Filed: Mar. 9, 2009

(65) Prior Publication Data

US 2009/0291879 A1   Nov. 26, 2009

Related U.S. Application Data

(62) Division of application No. 11/579,052, filed as application No. PCT/EP2005/004728 on Apr. 29, 2005, now abandoned.

(30) Foreign Application Priority Data

Apr. 30, 2004 (DK) ................................ 2004 00692

(51) Int. Cl.
*A61K 38/00* (2006.01)
*A61K 38/16* (2006.01)
*A61P 19/00* (2006.01)
*C07K 1/00* (2006.01)
*C07K 14/00* (2006.01)

(52) U.S. Cl. ........ 514/1.1; 514/17.1; 514/21.4; 530/350
(58) Field of Classification Search .................. None
See application file for complete search history.

(56) References Cited

FOREIGN PATENT DOCUMENTS

WO   WO/01/37861 A1   5/2001

OTHER PUBLICATIONS

Rapraeger, A.C. 2000. Syndecan-regulated receptor signaling. J. Cell Biol. 149:995-998.
Danilov, Y.N. and R.L.Juliano. 1989. Phorbol ester modulation of integrin-mediated cell adhesion: A post receptor event. J. Cell Biol. 108:1925-1933.
Wilcox-Adelman, S.A., F.Denhez, and P.F.Goetinck. 2002. Syndecan-4 modulates focal adhesion kinase phosphorylation. J. Biol. Chem. 277:32970-32977.
Iba, K., R.et al. 2000. The cysteine-rich domain of human ADAM 12 supports cell adhesion through syndecans . . . J. Cell Biol. 149:1143-1156.
Mansson, B., Wenglen, C., Morgelin, M., Saxne, T., and Heinegard, D. (2001) Association of Chondroherin with Collagen Type II. J.Biol. Chem. 276, 32883-32888.
Camper, L., Heinegård, D., and Lundgren-Åkerlund, E. (1997) Integrin alpha2beta1 is a receptor for the cartilage matrix protein chondroadherin. J.Cell Biol 138, 1159-1167.
Soummarin, Y. and Heinegard, D. (1983) Specific interaction between cartilage proteoglycans andhyaluronic acid at the chondrocyte cell surface. Biochem.J. 214, 777-784.
Mould, A. P., Burrows, L., and Humphries, M. J. (1998) Identification of amino acid residues that form part of the ligand-binding pocket of . . . J.Biol.Chem. 273, 25664-2567.
Koivunen, E., et al. (2001) Inhibition of beta2 integrin-mediated leukocyte cell adhesion by leucine-leucine-glycine motif-containing peptides. J.Cell Biol. 153, 905-916.
UniProt O15335 (CHAD_Human) Jun. 20, 2002.

*Primary Examiner* — Cherie M Woodward
(74) *Attorney, Agent, or Firm* — Lynn E. Barber

(57) ABSTRACT

A linear or cyclic peptide and the use of said peptide in medicine and especially in the manufacture of a medicament for the treatment and/or prophylaxis of a disease associated with inflammatory mediated cartilage destruction. The minimal core sequence of the linear or cyclic peptide is WLEAK (SEQ ID No. 1). Alternatives are WLEAR (SEQ ID NO. 17) and WLDAK (SEQ ID No. 18).

9 Claims, 16 Drawing Sheets

Adhesion of K9-cells to chondroaderin and collagen type II

Chondroadherin binding to heparin-sepharose

Western blot (anti 80)

Adhesion to CHAD

Adhesion to CII

Adhesion of bovine chondrocytes to chondroadherin

Figure 8
Adhesion to Peptide of Sequence ID No. 3
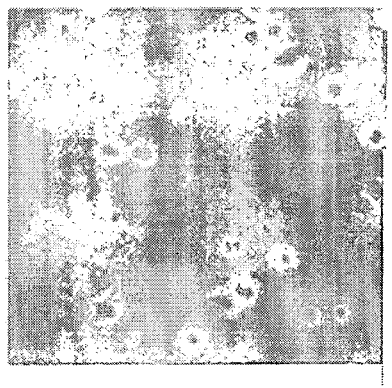
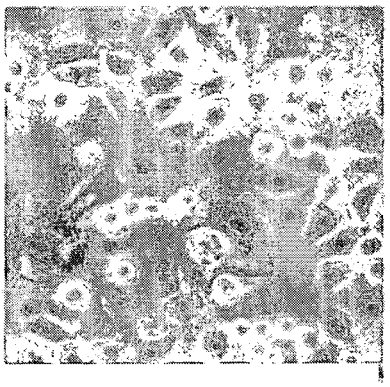
peptide coat
peptide coat and peptide in solution
Adhesion to Peptide of Sequence ID No. 7
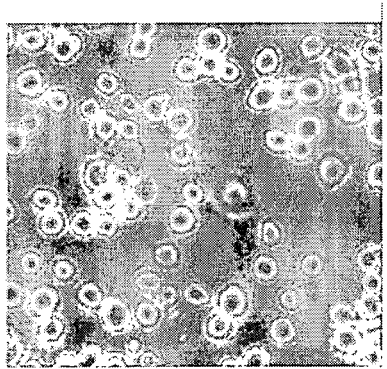
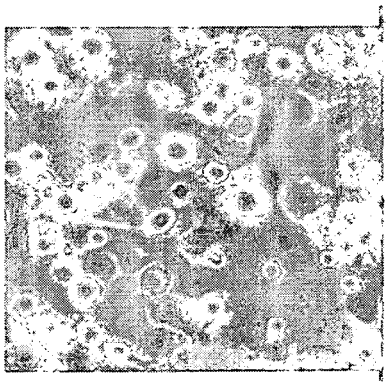
peptide coat
peptide coat and peptide in solution

SEQUENCE LISTING

```
<160> NUMBER OF SEQ ID NOS: 28

<210> SEQ ID NO 1
<211> LENGTH: 5
<212> TYPE: PRT
<213> ORGANISM: Homo sapiens

<400> SEQUENCE: 1

Trp Leu Glu Ala Lys
1               5

<210> SEQ ID NO 2
<211> LENGTH: 8
<212> TYPE: PRT
<213> ORGANISM: Homo sapiens

<400> SEQUENCE: 2

Leu Arg Arg Trp Leu Glu Ala Lys
1               5

<210> SEQ ID NO 3
<211> LENGTH: 12
<212> TYPE: PRT
<213> ORGANISM: Homo sapiens

<400> SEQUENCE: 3

Gln Leu Arg Gly Leu Arg Arg Trp Leu Glu Ala Lys
1               5                   10

<210> SEQ ID NO 4
<211> LENGTH: 5
<212> TYPE: PRT
<213> ORGANISM: Homo sapiens

<400> SEQUENCE: 4

Lys Arg Ser Lys Lys
1               5

<210> SEQ ID NO 5
<211> LENGTH: 6
<212> TYPE: PRT
<213> ORGANISM: Homo sapiens

<400> SEQUENCE: 5

Lys Lys Ala Gly Arg His
1               5

<210> SEQ ID NO 6
<211> LENGTH: 13
```

-continued

```
<212> TYPE: PRT
<213> ORGANISM: homo sapiens

<400> SEQUENCE: 6

Lys Phe Pro Thr Lys Arg Ser Lys Lys Ala Gly Arg His
1               5                   10

<210> SEQ ID NO 7
<211> LENGTH: 14
<212> TYPE: PRT
<213> ORGANISM: homo sapiens

<400> SEQUENCE: 7

Cys Lys Phe Pro Thr Lys Arg Ser Lys Lys Ala Gly Arg His
1               5                   10

<210> SEQ ID NO 8
<211> LENGTH: 338
<212> TYPE: PRT
<213> ORGANISM: homo sapiens

<400> SEQUENCE: 8

Ala Cys Pro Gln Asn Cys His Cys His Ser Asp Leu Gln His Val Ile
1               5                   10                  15

Cys Asp Lys Val Gly Leu Gln Lys Ile Pro Lys Val Ser Glu Lys Thr
            20                  25                  30

Lys Leu Leu Asn Leu Gln Arg Asn Asn Phe Pro Val Leu Ala Ala Asn
        35                  40                  45

Ser Phe Arg Ala Met Pro Asn Leu Val Ser Leu His Leu Gln His Cys
    50                  55                  60

Gln Ile Arg Glu Val Ala Ala Gly Ala Phe Arg Gly Leu Lys Gln Leu
65                  70                  75                  80

Ile Tyr Leu Tyr Leu Ser His Asn Asp Ile Arg Val Leu Arg Ala Gly
                85                  90                  95

Ala Phe Asp Asp Leu Thr Glu Leu Thr Tyr Leu Tyr Leu Asp His Asn
            100                 105                 110

Lys Val Thr Glu Leu Pro Arg Gly Leu Leu Ser Pro Leu Val Asn Leu
        115                 120                 125

Phe Ile Leu Gln Leu Asn Asn Asn Lys Ile Arg Glu Leu Arg Ala Gly
    130                 135                 140

Arg Phe Gln Gly Ala Lys Asp Leu Arg Trp Leu Tyr Leu Ser Glu Asn
145                 150                 155                 160

Ala Leu Ser Ser Leu Gln Pro Gly Ala Leu Asp Asp Val Glu Asn Leu
                165                 170                 175

Ala Lys Phe His Val Asp Arg Asn Gln Leu Ser Ser Tyr Pro Ser Ala
            180                 185                 190

Ala Leu Ser Lys Leu Arg Val Val Glu Glu Leu Lys Leu Ser His Asn
        195                 200                 205

Pro Leu Lys Ser Ile Pro Asp Asn Ala Phe Gln Ser Phe Gly Arg Tyr
    210                 215                 220

Leu Glu Thr Leu Trp Leu Asp Asn Thr Asn Leu Glu Lys Phe Ser Asp
225                 230                 235                 240

Gly Ala Phe Leu Gly Val Thr Thr Leu Lys His Val His Leu Glu Asn
                245                 250                 255

Asn Arg Leu Asn Gln Leu Pro Ser Asn Phe Pro Phe Asp Ser Leu Glu
            260                 265                 270

Thr Leu Ala Leu Thr Asn Asn Pro Trp Lys Cys Thr Cys Gln Leu Arg
        275                 280                 285
```

-continued

Gly Leu Arg Arg Trp Leu Glu Ala Lys Ala Ser Arg Pro Asp Ala Thr
    290                 295                 300

Cys Ala Ser Pro Ala Lys Phe Lys Gly Gln His Ile Arg Asp Thr Asp
305                 310                 315                 320

Ala Phe Arg Ser Cys Lys Phe Pro Thr Lys Arg Ser Lys Ala Gly
                325                 330                 335

Arg His

<210> SEQ ID NO 9
<211> LENGTH: 21
<212> TYPE: PRT
<213> ORGANISM: homo sapiens

<400> SEQUENCE: 9

Cys Gln Leu Arg Gly Leu Arg Arg Trp Leu Glu Ala Lys Ala Ser Arg
1               5                   10                  15

Pro Asp Ala Thr Cys
                20

<210> SEQ ID NO 10
<211> LENGTH: 52
<212> TYPE: PRT
<213> ORGANISM: homo sapiens

<400> SEQUENCE: 10

Ser Leu Glu Thr Leu Ala Leu Thr Asn Asn Pro Trp Lys Cys Thr Cys
1               5                   10                  15

Gln Leu Arg Gly Leu Arg Arg Trp Leu Glu Ala Lys Ala Ser Arg Pro
                20                  25                  30

Asp Ala Thr Cys Ala Ser Pro Ala Lys Phe Lys Gly Gln His Ile Arg
            35                  40                  45

Asp Thr Asp Ala
        50

<210> SEQ ID NO 11
<211> LENGTH: 14
<212> TYPE: PRT
<213> ORGANISM: homo sapiens

<400> SEQUENCE: 11

Gln Leu Arg Gly Leu Arg Arg Trp Leu Glu Ala Lys Ala Ser
1               5                   10

<210> SEQ ID NO 12
<211> LENGTH: 21
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (21)..(21)
<223> OTHER INFORMATION: AMIDATION

<400> SEQUENCE: 12

Cys Gln Leu Arg Gly Leu Arg Arg Trp Leu Glu Ala Lys Ala Ser Arg
1               5                   10                  15

Pro Asp Ala Thr Cys
                20

```
<210> SEQ ID NO 13
<211> LENGTH: 7
<212> TYPE: PRT
<213> ORGANISM: Homo sapiens

<400> SEQUENCE: 13

Cys Trp Leu Glu Ala Lys Cys
1               5

<210> SEQ ID NO 14
<211> LENGTH: 14
<212> TYPE: PRT
<213> ORGANISM: Homo sapiens

<400> SEQUENCE: 14

Cys Gln Leu Arg Gly Leu Arg Arg Trp Leu Glu Ala Lys Cys
1               5                   10

<210> SEQ ID NO 15
<211> LENGTH: 14
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (14)..(14)
<223> OTHER INFORMATION: AMIDATION

<400> SEQUENCE: 15

Cys Lys Phe Pro Thr Lys Arg Ser Lys Lys Ala Gly Arg His
1               5                   10

<210> SEQ ID NO 16
<211> LENGTH: 7
<212> TYPE: PRT
<213> ORGANISM: Homo sapiens

<400> SEQUENCE: 16

Cys Lys Arg Ser Lys Lys Cys
1               5

<210> SEQ ID NO 17
<211> LENGTH: 5
<212> TYPE: PRT
<213> ORGANISM: Homo sapiens

<400> SEQUENCE: 17

Trp Leu Asp Ala Lys
1               5

<210> SEQ ID NO 18
<211> LENGTH: 5
<212> TYPE: PRT
<213> ORGANISM: Homo sapiens

<400> SEQUENCE: 18

Trp Leu Glu Ala Arg
1               5

<210> SEQ ID NO 19
<211> LENGTH: 8
<212> TYPE: PRT
<213> ORGANISM: Homo sapiens

<400> SEQUENCE: 19
```

```
Gln Leu Arg Gly Leu Arg Arg Trp
1               5

<210> SEQ ID NO 20
<211> LENGTH: 8
<212> TYPE: PRT
<213> ORGANISM: Homo sapiens

<400> SEQUENCE: 20

Cys Gln Leu Arg Gly Leu Arg Arg
1               5

<210> SEQ ID NO 21
<211> LENGTH: 7
<212> TYPE: PRT
<213> ORGANISM: Homo sapiens

<400> SEQUENCE: 21

Ser Ser Val Tyr Gly Leu Arg
1               5

<210> SEQ ID NO 22
<211> LENGTH: 8
<212> TYPE: PRT
<213> ORGANISM: Homo sapiens

<400> SEQUENCE: 22

Ala Glu Ile Asp Gly Ile Glu Leu
1               5

<210> SEQ ID NO 23
<211> LENGTH: 7
<212> TYPE: PRT
<213> ORGANISM: Homo sapiens

<400> SEQUENCE: 23

Arg Arg Glu Thr Ala Trp Ala
1               5

<210> SEQ ID NO 24
<211> LENGTH: 9
<212> TYPE: PRT
<213> ORGANISM: Homo sapiens

<400> SEQUENCE: 24

Cys Pro Cys Phe Leu Leu Gly Cys Cys
1               5

<210> SEQ ID NO 25
<211> LENGTH: 9
<212> TYPE: PRT
<213> ORGANISM: Homo sapiens

<400> SEQUENCE: 25

Ile Pro Lys Val Ser Glu Lys Thr Lys
1               5

<210> SEQ ID NO 26
<211> LENGTH: 13
<212> TYPE: PRT
<213> ORGANISM: Homo sapiens

<400> SEQUENCE: 26

Phe Ser Asp Gly Ala Phe Leu Gly Val Thr Thr Leu Lys
1               5                   10
```

```
<210> SEQ ID NO 27
<211> LENGTH: 15
<212> TYPE: PRT
<213> ORGANISM: homo sapiens

<400> SEQUENCE: 27

Leu Arg Val Val Glu Glu Leu Lys Leu Ser His Asn Pro Leu Lys
1               5                   10                  15

<210> SEQ ID NO 28
<211> LENGTH: 15
<212> TYPE: PRT
<213> ORGANISM: Homo sapiens

<400> SEQUENCE: 28

Cys Thr Cys Gln Leu Arg Gly Leu Arg Arg Trp Leu Glu Ala Lys
1               5                   10                  15
```

MODULATION OF CARTILAGE HOMEOSTASIS BY ACTIVE DOMAINS OF CELL BINDING EXTRACELLULAR MATRIX MOLECULES

CROSS-REFERENCE TO RELATED APPLICATIONS

This application is a divisional application of U.S. application Ser. No. 11/579,052 filed Dec. 26, 2006 (now abandoned), which claims priority from PCT/EP05/04728 (Apr. 29, 2005), claiming priority from Denmark PA 2004 00692 (Apr. 30, 2004).

FIELD OF THE INVENTION

The invention relates to a method for treatment and/or prophylaxis of a disease associated with tissue changes such as, e.g. an inflammatory joint disease such as, e.g., rheumatoid arthritis, psoriatic arthritis, juvenile chronic arthritis, systemic lupus erythematosus (SLE), infectious arthritis and juvenile idiopathic arthritis, other diseases involving joint structures such as, e.g., osteoarthritis, meniscal damage, gout, diseases affecting structural elements of the musculoskeletal system such as, e.g., tendon damage, ligament damage, and bone disease such as, e.g., osteoporosis, diseases affecting major arteries including atherosclerosis, vasculitis and trauma leading to injury, lung diseases including asthma and Chronic Obstructive Pulmonary Disease (COPD). The invention also relates to novel compounds for use in such a method and compositions, and in a preferred aspect the invention relates to novel peptide compounds with the core peptide sequence WLEAK (SEQ ID No. 1).

In the current context the type of tissue changes of main interest is changes involved with inflammatory mediated cartilage destruction.

In further aspects the invention relates to compounds that interact with a receptor such as, e.g., an integrin receptor and/or a polyanionic structure such as, e.g., heparin/heparan sulfate.

BACKGROUND

Destruction of tissues is a feature of diseases affecting many organ types and represents an increasing problem to the population with particular emphasis on the aging. Many of these diseases have an element of chronic inflammation. Examples of such diseases are rheumatoid arthritis, osteoarthritis, osteoporosis, artheriosclerosis, chronic lung diseases, tendinitis, spine problems with lower back pain and intervertebral disc hernia. These diseases encompass by far the largest expenditure among major disease categories for society and suffering for individuals.

Arthritis is a common name for several inflammatory joint diseases. Joint diseases are extremely common in the population. While rheumatoid arthritis sufferers represent some 1%, osteoarthritis is much more common with an incidence of at least some 10%. Major features of the two disease entities are progressive destruction of joint structures as well as inflammation causing pain and disability.

At present, the symptoms of conditions such as rheumatoid arthritis can for some patients be alleviated by medical treatment, e.g. anti-inflammatory agents including corticosteroids, physiotherapy or surgery. More recent use of inhibitors of cytokines, particularly TNF-α has improved the situation for two-thirds of the patients with severe rheumatoid arthritis. However, many patients do not effectively respond to the above-mentioned treatments or the treatments lead to a number of undesired side-effects (see e.g. Smolen & Steiner, Nature Reviews, Vol. 2, (2003), 473-488)

It is known in the art that chondroadherin (CHAD) conjugated with additional compounds has an effect on tissue changes (WO0137861) and it has also been shown that collagen II in combination with chondroadherin (WO03049669) could be used for treating intervertebral discs. The present invention shows to our surprise that chondroadherin and fragments thereof as pure compounds have a desired effect in removing and/or inhibit parameters related to tissue damaging diseases.

There is a need for new approaches with respect to treatment of diseases associated with tissue changes, especially with a view to the efficiency of the treatment and to reduction of side-effects.

Other objects and advantages will be more fully apparent from the following disclosure and appended claims.

SUMMARY OF THE INVENTION

The invention herein is a linear or cyclic peptide and the use of said peptide in medicine and especially in the manufacture of a medicament for the treatment and/or prophylaxis of a disease associated with inflammatory mediated cartilage destruction. The minimal core sequence of the linear or cyclic peptide is WLEAK (SEQ ID No. 1).

BRIEF DESCRIPTION OF THE DRAWINGS

FIG. 8 shows adhesion of k105 cells to cell binding peptides.

DESCRIPTION OF THE INVENTION

Figure 1:
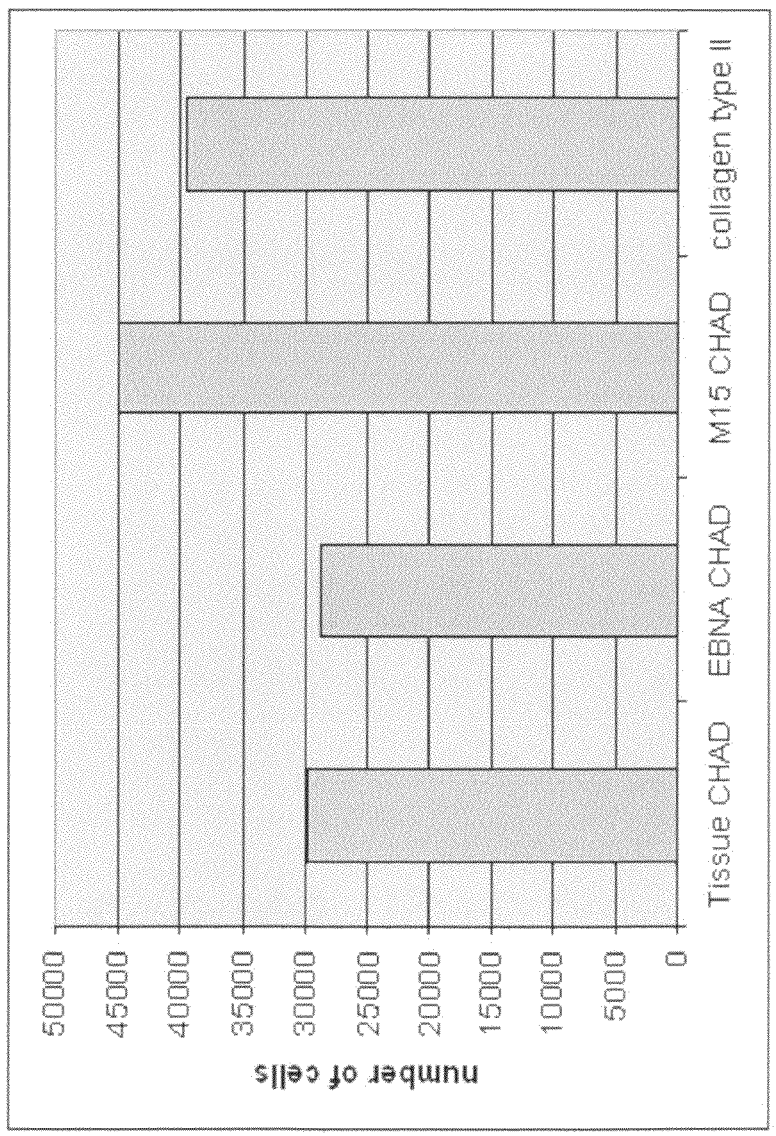
FIG. 1 is a bar-graph showing number of cells adhering to substrates chondroadherin and collagen.

The present invention provides a linear or cyclic peptide and methods of use thereof. In general, the invention herein is for use of a linear or cyclic peptide having the formula 1

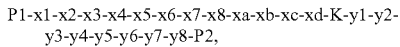
P1-x1-x2-x3-x4-x5-x6-x7-x8-xa-xb-xc-xd-K-y1-y2-y3-y4-y5-y6-y7-y8-P2, wherein xa is selected from W, K or Y,
xb is selected from L or R,
xc is selected from E or S,
xd is selected form A, K, D or E
x1 is selected from C or absent
x2 is selected from Q or absent
x3 is selected from L or absent
x4 is selected from R, C or absent
x5 is selected from G, K or absent
x6 is selected from L, F or absent
x7 is selected from R, P or absent
x8 is selected from R, C, T or absent
y1 is selected from A, C or absent
y2 is selected from S, G or absent
y3 is selected from R or absent
y4 is selected from P, H or absent
y5 is selected from D or absent
y6 is selected from A or absent
y7 is selected from T or absent
y8 is selected from C or absent
and P1 and P2 are absent or a protective group,
in the manufacture of a medicament for the treatment and/or prophylaxis of a disease associated with inflammatory mediated cartilage destruction, including an inflammatory joint disease such as, e.g., rheumatoid arthritis, psoriatic arthritis, juvenile chronic arthritis, systemic lupus erythematosus (SLE), infectious arthritis and juvenile idiopathic arthritis, other diseases involving joint structures such as, e.g., osteoarthritis, meniscal damage, gout, diseases affecting structural elements of the musculoskeletal system such as, e.g., tendon damage, ligament damage and bone disease such as, e.g., osteoporosis, diseases affecting major arteries including atherosclerosis.

Three specific embodiments of the invention herein include use of this linear or cyclic peptide wherein P1 is acetyl or absent and P2 is an amide or absent; wherein x2-x3 is selected from Q-L or absent and y5-y6-y7 is D-A-T or absent; and wherein x4-x5-x6-x7 is selected from R-G-L-R, C—K—F—P or absent and y2-y3-y4 is selected from S—R—P, G-R—H or absent.

More specifically, formula 1 preferably may be KRSKK (SEQ ID No. 4), CKRSKKC (SEQ ID No. 16), KFPTKRSKKAGRH (SEQ ID No. 6), CKFPTKRSKKAGRH (SEQ ID No. 7) or its protected form (SEQ ID No. 15). In formula 1, in further preferred embodiments, xa is selected from W or T and xb is L, xc is E and xd is selected from A or E, and most preferably in these embodiments, xa is W and xb is L, xc is E and xd is A.

Thus, most preferably, formula 1 is WLEAK (SEQ. ID No. 1), LRRWLEAK (SEQ. ID No. 2), QLRGLRRWLEAK (SEQ. ID. No. 3), QLRGLRRWLEAKAS (SEQ. ID. No. 11), CWLEAKC (SEQ. ID. No. 13), CQLRGLRRWLEAKASR-PDATC (SEQ ID No. 9) or its protected form (SEQ ID No.12), CQLRGLRRWLEAKC (SEQ ID No. 14).

The invention further includes linear or cyclic peptides having the formula 1 as set forth above in its general and specific embodiments, as well as uses of the peptides of the invention in medicine, or with one or more adjutants, carriers or excipients, and a method for the treatment and/or prophylaxis of inflammatory mediated cartilage destruction in vivo comprising administering to the subject in need thereof an effective amount of a compound as defined herein.

Accordingly, the present invention provides a method for the treatment and/or prophylaxis of a disease associated with tissue changes, such as, e.g. an inflammatory joint disease such as, e.g., rheumatoid arthritis, psoriatic arthritis, juvenile chronic arthritis, systemic lupus erythematosus (SLE), infectious arthritis and juvenile idiopathic arthritis, other diseases involving joint structures such as, e.g., osteoarthritis, meniscal damage, gout, diseases involving the intervertebral disc of the spine, such as, e.g., lower back pain, diseases affecting structural elements of the musculoskeletal system such as, e.g., tendon damage, ligament damage, and bone disease such as, e.g., osteoporosis, diseases affecting major arteries including atherosclerosis, vasculitis and trauma leading to injury, lung diseases including asthma and COPD. The method comprising administering to a subject in need thereof a therapeutic and/or prophylactic amount of a compound capable of at least one of the following:

a) modulating changes of the phenotype of cells involved in a disease associated with tissue changes,
b) regulating the production of extracellular matrix molecules by cells involved in a disease associated with tissue changes,
c) inhibiting the normal production and activity of catabolic factors, such as, e.g., NO, cytokines and/or proteinases of cells involved in a disease associated with tissue changes,
d) regulating division of cells involved in a disease associated with tissue changes,
e) regulating migration of cells involved in a disease associated with tissue changes,
f) regulating the production of growth factors and/or
g) regulating the response of cells involved in a disease associated with tissue changes to external stimuli.

The general purpose of the method according to the invention is to direct the cells into performing specific actions, all of which have a positive effect on a disease associated with tissue changes.

In the current context the type of tissue changes of main interest is changes involved with inflammatory mediated cartilage destruction. The type of cells involved in a disease associated with tissue changes depends on the disease in question and the affected tissues. Examples of cells involved in a disease as described above are chondrocytes, osteoblasts, osteocytes, fibroblasts, tenocytes, smooth muscle cells, macrophages and pro-inflammatory cells like synovial fibroblasts and dendritic cells.

In a specific embodiment, the cells involved in the diseases are chondrocytes. The following description of the method above is generally given for all type of cells involved in a disease associated with tissue changes, but with references to specific cells, such as, e.g. chondrocytes and smooth muscle cells and how the behavior of these cells should be regulated in order to treat or prevent a tissue change relating to chondrocytes.

In a specific aspect, a method according to the invention comprises administering to a subject in need thereof a therapeutic and/or prophylactic amount of a compound capable of modulating changes of the phenotype of cells involved in a disease associated with tissue changes, item a. A specific definition of the term "phenotype" in the present context is not simple and a person skilled in the art will understand that the term relates to the character of the cell and can be defined at many levels. The simplest and traditionally used parameter is cell shape. Other ways of identifying phenotypes are by e.g.

the cells' production of molecules such as production of distinct patterns of matrix proteins, proteinases and growth factors, identification of stationary, migratory, catabolic and/or anabolic states of the cells, and identification of whether cells are dividing or non-dividing. Accordingly, the compound for use according to the invention may solely affect the phenotype of the cells. However, in a specific embodiment of the invention at least one other factor may be influenced by use of a compound according to the invention without—as a main effect—having effect on the phenotype of the cells. An example includes e.g. by regulating the production of growth factors.

Without being bound to any specific theory, the inventors have in a specific experiment found that especially a rounded shape of chondrocytes correlates to the cell behavior.

With respect to item b in the method according to the invention, one of the processes leading to tissue changes, such as tissue destruction, is failure to repair tissue damage. Although the tissue often responds by an increased production of some matrix constituents, it is becoming increasingly clear that there is a lack of a coordinated production of all the components needed for proper assembly of tissue structures. The outcome seems to be an inhibited assembly, which is even worse than an insufficiently active repair process. Thus, by regulating the production of extracellular matrix components a proper assembly of tissue structures may be obtained.

Item c of the method according to the invention: Another of the processes that leads to tissue changes is an increased breakdown of tissue structural molecules leading to tissue failure and destruction. This may be accomplished e.g. by proteinases produced by the tissue cells themselves. In all tissues with a component of tissue destruction, there is an increased proteinase production. By stimulating the cells to decrease the production of proteinases, the breakdown of tissue structural molecules may be prevented. As will be described in further details below, binding of specific ligands to a receptor such as, e.g. an integrin receptor, on chondrocytes will lead to a decrease in production of proteinases.

Item d of the method according to the invention: When cells are proliferating, the production of matrix components by the cells is at a minimum, i.e. the cells are not contributing to the repair of tissues. Accordingly, by preventing cell division, the focus of the cells may be shifted to production of matrix components and tissue repair. Cell division is believed to be dependent on the activity of integrin receptors, i.e. by regulating the activity of an integrin receptor by adding ligands that either stimulates or inhibits the receptor, cell division may be regulated.

Item e according to the invention: A way of treating a disease associated by tissue changes is to inhibit the migration of cells involved in such a disease. In e.g. athreriosclerosis there can be a migration of smooth muscle cells into the arterial intima. Theses cells will accumulate and many of them will divide. At the same time, fat builds up within these cells and around them and they also form connective tissue. Accordingly, the innermost layer of the artery becomes markedly thickened by these accumulating cells and surrounding material. If the wall is thickened sufficiently, the lumen of the artery will be reduced and the blood flow decreased, thus decreasing the oxygen supply. Cell migration is believed to be dependent on the activity of integrin receptors, i.e. by regulating the activity of an integrin receptor by adding ligands that interacts with the receptor, cell migration may be inhibited.

The present inventors have found that inhibition of chondrocyte cell migration in specific situations is advantageous for ameliorating diseases associated with tissue changes.

Item f of a method according to the invention: Another entry point for the treatment of a disease associated with tissue changes is the regulation of production of growth factors. Growth factors are gene products playing important roles in the regulation of e.g. cell division, tissue proliferation and production of matrix constituents. Each growth factor has a specific cell-surface receptor and binding of a growth factor to its receptor may initiate or, in some cases, block cell division. Too high levels of a particular growth factor, tgf-beta, has been shown to induce the changes seen in osteoarthritis, and tgf-beta levels are also high in lung fibrosis leading to excessive collagen production.

More specifically, the compounds for use in a method according to the invention, mediates their actions on the cells associated with the diseases mentioned above by interacting with structures on the cell surface of the cells. Examples of such structures are receptors and/or polyanionic structures, particularly heparinoids including heparin and heparan sulphate. Thus, the invention relates to a method wherein the one or more compounds are capable of a) interacting with a receptor expressed at a surface of a cell involved in a disease associated with tissue changes,
b) interacting with polyanionic structures, such as, but not limited to heparan sulfate, expressed at or present on a surface of a cell involved in a disease associated with tissue changes, and/or
c) combined interactions with one or more receptor and/or one or more polyanionic structure.

In the method a compound is capable of interacting with both a receptor and with a polyanionic structure, or with two or more receptors and/or two or more polyanionic structures. Receptors often need to polymerize for optimal activity, i.e. by providing one compound capable of crosslinking two or more receptors or polyanionic structures, dimerization or polymerization is ensured, leading to optimal activity. Furthermore, binding of a compound to a receptor and/or polyanionic structure will be increased, as binding is tighter when two or more binding points are involved. For example, chondroadherin is believed to have two specific binding domains, one for the receptor integrin and the other for heparinoid binding. Accordingly, such substances may have more than one functionality.

The chondrocytes, being the only type of cell in cartilage, have a key function in cartilage homeostasis. The roles of chondrocytes include normal turnover of matrix molecules and deposition of molecules into functioning matrix.

Studies by the present inventors have shown that chondrocytes express several cell surface structures that are relevant for the regulation of the cells.

Relevant cell surface structures include the integrin receptors. The integrin receptor is a complex of one alpha and one beta chain, which may be chosen from 18 different alpha chains and 8 different beta chains. The various integrin receptors may have different ligands and elicit different responses.

Another example of cell surface structures on chondrocytes, which are relevant for the regulation of the cells, is polyanionic structures such as, e.g. heparinoids like heparin/heparan sulfate, chondroitin/dermatan sulfate chains, or clusters of sulphated gangliosides or phospholipids.

The heparinoid heparan sulfate is ubiquitous at the cell surface, where it predominantly may be found on proteoglycans of either the transmembrane syndecan family or the glycosylphosphatidylinositol (GPI)-anchored glypican family.

In the text herein, the term heparinoid also include heparinoid mimics.

The present inventors have found that chondroadherin inhibits the binding of cells to the integrin $\alpha_2\beta_1$ receptor on chondrocytes, strongly indicating that chondroadherin binds to chondrocytes via the integrin $\alpha_2\beta_1$ receptor. Chondroadherin is a leucine-rich, cartilage matrix protein. The binding of chondroadherin induces the cells to maintain a rounded shape and stay in an anabolic mode, appears to stimulate the cells to production of ECM-molecules, and prevents cell spreading and/or migration as well as cell division. Studies have also shown that most other natural integrin ligands, such as, e.g. collagen II have the almost opposite effects on the cells.

As shown herein human chondrocytic cells adhere equally well to native as to unfolded chondroadherin showing that a linear peptide sequence is mediating the adhesion. Digestion of chondroadherin has also shown that smaller fragments of chondroadherin are capable of mediating the effects mentioned above.

Accordingly, in one specific embodiment of the invention the receptor a) is an integrin receptor and the one or more compounds are peptides which may comprise one or more chondroadherin fragments or analogs thereof.

The present inventors have identified a specific fragment of chondroadherin (CQLRGLRRWLEAK—SEQ ID NO. 3), which is contemplated upon binding to chondrocytic cells via an integrin receptor, such as, e.g. the integrin $\alpha_2\beta_1$ receptor, to have the effects on the chondrocytes as described above, i.e. prevents spreading and migration of the cells and at the same time the cells tend to maintain the rounded phenotype. Further studies have shown that a sub fragment LRRWLEAK (SEQ ID NO. 2) similarly to CQLRGLRRWLEAK (SEQ ID NO. 3) prevents cell spreading and migration and maintain the rounded shape of the cells. The activity for integrin binding is located in the C-terminal residues of the sequence, involving the WLEAK sequence (SEQ ID NO. 1). The inventors have found that the integrin binding properties of the sequence are lost if lysine is exchanged with another amino acid with a basic side chain, namely arginine, i.e. the lysine in the WLEAK (SEQ ID No. 1) sequence is necessary for activity. However, it cannot be ruled out, that a sequence wherein lysine is exchanged with another amino acid may maintain its activity.

The inventors have also found, that the exchange of tryptophan for another amino acid with an aromatic side chain, namely tyrosine and the exchange of glutamic acid for another acidic amino acid, namely aspartic acid, do not have any influence on the integrin binding activity of the sequence.

Accordingly, the present invention relates to a method, wherein at least one of the chondroadherin fragments has at least about 60% such as at least about 70%, at least about 75%, at least about 80%, at least about 85%, at least about 90% or at least about 95% identity to the amino acid sequence of SEQ ID No: 1 (WLEAK).

An example of a sequence having at least 60% identity to SEQ ID No: 1 is the following sequence:

Xaa-L-Yaa-A-K, wherein Xaa may be chosen from tryptophan and tyrosin, and Yaa may be chosen from glutamic acid and aspartic acid The invention also relates to a method, wherein at least one of the chondroadherin fragments has at least about 75% such as at least about 80%, at least about 85%, at least about 90% or at least about 95% identity to the amino acid sequence of SEQ ID No: 2 (LRRWLEAK).

Furthermore, the invention relates to a method, wherein at least one of the chondroadherin fragments has at least about 75% such as at least about 80%, at least about 85%, at least about 90% or at least about 95% identity to the amino acid sequence of SEQ ID No: 3 (QLRGLRRWLEAK).

The inventors have also found that binding of chondroadherin to syndecan on the cell surfaces prevents cell division, and leads to increased adhesion.

The syndecans are a family of four transmembrane heparan sulfate proteoglycans, which are recognized as important cell surface adhesion co-receptors that actively participate in adhesion and signaling.

Chondroadherin binds to syndecan via the heparin/heparan sulfate chains. The present inventors have identified a specific fragment of chondroadherin, which interact with heparin/heparan sulfate.

Accordingly, the present invention relates to a method, wherein at least one of the chondroadherin fragments has at least about 75% such as at least about 80%, at least about 85%, at least about 90% or at least about 95% identity to the amino acid sequence of SEQ ID No: 4 (KRSKK).

The invention also relates to a method, wherein at least one of the chondroadherin fragments has at least about 75% such as at least about 80%, at least about 85%, at least about 90% or at least about 95% identity to the amino acid sequence of SEQ ID No: 5 (KKAGRH).

Moreover, the invention also relates to a method, wherein at least one of the chondroadherin fragments has at least about 75% such as at least about 80%, at least about 85%, at least about 90% or at least about 95% identity to the amino acid sequence of SEQ ID No: 6 (KFPTKRSKKAGRH).

Furthermore, the invention relates to a method, wherein at least one of the chondroadherin fragments has at least about 75% such as at least about 80%, at least about 85%, at least about 90% or at least about 95% identity to the amino acid sequence of SEQ ID No: 7 (CKFPTKRSKKAGRH).

In another embodiment, the peptide according to the invention comprises at least one chondroadherin fragment capable of binding the integrin receptor, and at least one chondroadherin fragment capable of binding to heparin/heparan sulfate in order to modulate signaling, wherein heparin/heparan sulfate may be found on the extracellular domains of syndecans and glypicans.

In a specific example the peptide comprises an amino acid sequence having at least about 75% such as at least about 80%, at least about 85%, at least about 90% or at least about 95% identity to
i) one of the amino acid sequences of SEQ ID NO. 1, SEQ ID NO. 2 or SEQ ID NO. 3, and
ii) one of the amino acid sequences of SEQ ID NO. 4, SEQ ID NO. 5 or SEQ ID NO. 6.

In connection with amino acid sequences, "sequence identity" refers to sequences which have the stated value when assessed using e.g. using the SWISS—PROT protein sequence databank using FASTA pep-cmp with a variable pamfactor, and gap creation penalty set at 12.0 and gap extension penalty set at 4.0, and a window of 2 amino acids. Sequence identity at a particular residue is intended to include identical residues, which have simply been derivatized.

As mentioned above, studies have shown that linear fragments of chondroadherin interact strongly with their cell surface structures. For other peptides and cell surface structures, the interaction may be better if the peptides are non-linear.

In order to make more stable peptides, the peptides may be designed to be cyclic, as cyclic peptides are more resistant to exo-peptidases. In addition, protecting groups such as acetyl, amide or methyl, tools well known in the art, are synthetic modifications, which further help to stabilize peptides against decomposition and metabolic degradation.

The present invention particularly provides a novel linear or cyclic peptide of the general Formula (I) and their uses:

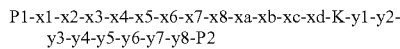

FORMULA I

Wherein xa is selected from W, K or Y
Wherein xb is selected from L or R
Wherein xc is selected from E or S
Wherein xd is selected form A, K, D or E
Wherein x1 is selected from C or absent
Wherein x2 is selected from Q or absent
Wherein x3 is selected from L or absent
Wherein x4 is selected from R, C or absent
Wherein x5 is selected from G, K or absent
Wherein x6 is selected from L, F or absent
Wherein x7 is selected from R, P or absent
Wherein x8 is selected from R, C, T or absent
Wherein y1 is selected from A, C or absent
Wherein y2 is selected from S, G or absent
Wherein y3 is selected from R or absent
Wherein y4 is selected from P, H or absent
Wherein y5 is selected from D or absent
Wherein y6 is selected from A or absent
Wherein y7 is selected from T or absent
Wherein y8 is selected from C or absent
Wherein P1 and P2 are absent or a protective group
or a pharmaceutically active salt thereof, in the manufacture of a medicament for the treatment and/or diagnosis of diseases, disorders related to tissue changes associated with inflammatory mediated cartilage destruction.

In another embodiment, the invention relates to novel peptides as further exemplified in the appended claims whereto reference is made. An analogous discussion as given above is also relevant for these peptides.

Pharmaceutical Compositions

The invention also relates to a pharmaceutical composition comprising a compound capable of
  a) modulating changes of the phenotype of cells involved in a disease associated with tissue changes,
  b) regulating the production of extracellular matrix molecules by cells involved in a disease associated with tissue changes,
  c) inhibiting the normal production and activity of catabolic factors, such as, e.g., NO, cytokines and/or proteinases of cells involved in a disease associated with tissue changes,
  d) regulating division of cells involved in a disease associated with tissue changes,
  e) regulating migration of cells involved in a disease associated with tissue changes,
  f) regulating the production of growth factors, and/or
  g) regulating the response of cells involved in a disease associated with tissue changes to external stimuli together with one or more pharmaceutical excipients.

Furthermore, the invention relates to a pharmaceutical composition comprising a compound capable of
  a) interacting with a receptor expressed at a surface of a cell involved in a disease associated with tissue changes,
  b) interacting with polyanionic structures expressed at or present on a surface of a cell involved in a disease associated with tissue changes, and/or
  c) combined interactions with one or more receptor and/or one or more polyanionic structure.
together with one or more pharmaceutical excipients.

In one embodiment the receptor is an integrin receptor.

The pharmaceutical compositions according to the invention normally comprise the specific compound together with one or more physiologically acceptable excipients, i.e. a therapeutically inert substance or carrier.

The carrier may take a wide variety of forms depending on the desired dosage form and administration route.

The pharmaceutically acceptable excipients may be e.g. fillers, binders, disintegrants, diluents, glidants, solvents, emulsifying agents, suspending agents, stabilizers, enhancers, flavors, colors, pH adjusting agents, retarding agents, wetting agents, surface active agents, preservatives, antioxidants etc. Details can be found in pharmaceutical handbooks such as, e.g., Remington's Pharmaceutical Science or Pharmaceutical Excipient Handbook. In those cases, where the pharmaceutical composition is intended for controlled release, it may also comprise release controlling agents such as, e.g., material normally used in the formulation of matrix tablets (e.g. cellulose derivatives like hydroxypropyl methylcellulose and the like). Alternatively, the composition may be coated with a controlled release coating such as an enteric coating or a film coating. A suitable coating may be a substantially water-insoluble but water-permeable coating.

The compound may be administered by any suitable route, such as, e.g. the oral, buccal, nasal, ocular, pulmonary, topical, transdermal, vaginal, rectal, ocular, parenteral (including inter alia subcutaneous, intramuscular, intraaricular and intravenous), route in a dose that is effective for the individual purposes. A person skilled in the art will know how to chose a suitable administration route.

The pharmaceutical composition comprising a compound according to the invention may be in the form of a solid, semi-solid or fluid composition.

The solid composition may be in the form of tablets such as, e.g. conventional tablets, effervescent tablets, coated tablets, melt tablets or sublingual tablets, pellets, powders, granules, granulates, particulate material, solid dispersions or solid solutions.

A semi-solid form of the composition may be a paste, cream, ointment, a gel or a hydrogel.

The fluid form of the composition may be a solution, an emulsion including nano-emulsions, a suspension, a dispersion, a liposomal composition, a spray, a mixture, a syrup or an elixir.

Other suitable dosages forms of the pharmaceutical compositions according to the invention may be vagitories, suppositories, plasters, patches, tablets, capsules, sachets, troches, devices etc.

The pharmaceutical compositions may be prepared by any of the methods well known to a person skilled in pharmaceutical formulation.

The invention also relates to use of a compound capable of
  a) modulating changes of the phenotype of cells involved in a disease associated with tissue changes,
  b) regulating the production of extracellular matrix molecules by cells involved in a disease associated with tissue changes,
  c) inhibiting the normal production and activity of catabolic factors, such as, e.g., NO, cytokines and/or proteinases of cells involved in a disease associated with tissue changes,
  d) regulating division of cells involved in a disease associated with tissue changes,
  e) regulating migration of cells involved in a disease associated with tissue changes,
  f) regulating the production of growth factors, and/or
  g) regulating the response of cells involved in a disease associated with tissue changes to external stimuli for the preparation of a pharmaceutical composition for the treatment and/or prophylaxis of a disease associated with tissue changes.

The invention furthermore relates to use of compound capable of
a) interacting with a receptor expressed at a surface of a cell involved in a disease associated with tissue changes,
b) interacting with polyanionic structures expressed at or present on a surface of a cell involved in a disease associated with tissue changes, and/or
c) combined interactions with one or more receptor and/or one or more polyanionic structure.

The receptor is an integrin receptor.

The interaction between the compound and the integrin receptor may be detected by any suitable method. One example of a suitable method is microscopic analysis of the cells in order to determine any alterations of cell shape. Another detection method involved detection of alterations in cell behavior.

Another method for detection of binding between a compound and an integrin receptor includes the addition of the compound in question to a assay comprising cells expressing the integrin receptor and a immobilized natural ligand to the integrin receptor, and evaluation of whether the compound inhibit binding of the cells to the natural ligands.

Binding can also be determined by FACS analyses of tagged peptide, and plasmon resonance (Biacore).

The interaction between the compound and the polyanionic structure may be detected by any suitable method. One example of a suitable method is microscopic analysis of the cells in order to determine any alterations of cell shape. Another detection method involved detection of alterations in cell behavior, such as, e.g. cell migration.

Another method for detection of binding between a compound and an polyanionic cell surface structure includes the addition of the compound in question to a assay comprising cells expressing polyanionic structure and a immobilized natural ligand to the polyanionic structure, and evaluation of whether the compound inhibit binding of the cells to the natural ligand.

Binding can also be determined by FACS analyses of tagged peptide, and isothermal titration colometry (ITC).

The invention also relates to an in vitro method for testing the activity of a compound or a combination of two or more compounds with respect to production of extracellular matrix constituents, the method comprising:
a) culturing cells in the presence of the one or more compounds to be tested,
b) monitoring release of matrix components from cultured tissue explants,
c) monitoring modified release of matrix components from cultures of tissue explants stimulated with catabolic agents, such as, e.g. IL-1 and fibronectin fragments,
d) monitoring modified release of matrix components from tissue explants cultured in the presence of growth factors,
e) monitoring modulation of progression of model disease in animals, e.g. collagen arthritis, bleomycin lung fibrosis and development of osteoarthritis.

EXAMPLES

The following examples are intended to illustrate the invention without limiting it thereto.

To obtain evidence that chondroadherin-derived peptides modulate changes of the phenotype of cells involved in a disease associated with tissue changes, we have performed experiments with such cells (chondrocytes, synoviocytes), and in cartilage explants and an arthritis animal model.

Materials and Methods

Expression and Purification of Recombinant Protein

Human chondroadherin cDNA was ligated into the pQE8 vector (QIAGEN Inc. Valencia, Calif.) and expressed in M15 E. coli. Overnight cultures (8 ml) of stationary phase bacteria were used to inoculate 400 ml LB-medium (Luria-Bertani) and the cells were allowed to grow for 2.5 hour at 37° C. ($OD_{600}$ of 0.7-0.9). Protein expression was induced by the addition of 2 mM IPTG (isopropyl-β-D-thiogalactopyranoside), (Sigma Chemicals CO., St Louis, Mo.) and the culture was grown for another 4.5 hour. Bacteria were then collected by centrifugation, frozen and resuspended in lysis buffer (6M GuHCl, 0.1M $NaH_2PO_4$ and 0.5M NaCl, pH 8.0) containing 5 mM NEM (Sigma). The suspension was passed 10 times through a 21 gauge needle (21 G, 0.8×50) to lyse the cells. Insoluble debris was removed by centrifugation. His-tagged recombinant protein was purified using a Hi-Trap Ni-chelating column (Pharmacia LKB Biotechnology, Uppsala, Sweden) essentially according to instructions from the manufacturer. The lysate was applied to the $Ni^{2+}$-charged column, washed with 10 volumes of lysis buffer and bound protein was eluted with 8M Urea, 0.1M $NaH_2PO_4$ and 0.5M NaCl pH 6.3. Fractions were immediately neutralized by the addition of 1M Tris pH 9.0. Fractions containing the desired protein as determined by SDS-PAGE and western blotting (data not shown) were pooled, dialyzed against water and lyophilized. EBNA-cell expressed chondroadherin was produced as described elsewhere (8).

Generation of Chondroadherin Peptides

Intact recombinant protein (1 mg, EBNA-cell expressed (8)) was proteolytically digested with Lys-C (Roche Molecular Biochemicals) at an enzyme to substrate ratio of 1:50 according to the instructions of the manufacturer. Generated peptides were separated by reversed phase chromatography on a Sephasil C8 column (Pharmacia LKB Biotechnology, Uppsala, Sweden) with a gradient of 0-70% acetonitrile, 0.1% TFA (0.1 ml/min. over 50 min.) using a SMART-System (Pharmacia LKB Biotechnology). The effluent was monitored for absorbance at 280 nm. Fractions were pooled, lyophilized and resuspended in PBS and then used in cell adhesion experiments to block adhesion to intact chondroadherin.

Mass Spectrometry

Mass spectrometry was performed using a Bruker Scout 384 Reflex III matrix-assisted laser desorption/ionization time-of-flight (MALDI-TOF) mass spectrometer. The instrument was used in the positive ion mode with delayed extraction and an acceleration voltage of 26 kV. Peptide samples were mainly analyzed using the reflector detector and 50-150 single-shot spectra were accumulated for improved signal to noise ratio. The software used to identify the obtained peptide masses was ProFound.

Synthetic Peptides

Polypeptides as described herein may be prepared by any conventional modes of synthesis, including chemical synthesis or recombinant DNA technology. Chemical synthesis may be performed by methods well known in the art involving cyclic sets of reactions of selective deprotection of the functional groups of a terminal amino acid and coupling of selectively protected amino acids, followed by complete deprotection of all functional groups. Synthesis may be performed in solution or on a solid support using suitable solid phases known in the art. Preferably the polypeptides are substantially purified, e.g. pyrogen-free, e.g. more than 70%, especially preferably more than 90% pure (as assessed for example, in the case of peptides, by an appropriate technique such as peptide mapping, sequencing or chromatography). Purification may be performed for example by chromatography (e.g. HPLC, size-exclusion, ion-exchange, affinity, hydrophobic interaction, reverse-phase) or capillary electrophoresis.

Heparin Binding

Intact recombinant protein (10 µg, EBNA-cell expressed) diluted in PBS was passed over Heparin-Sepharose (Amersham Pharmacia) (1 ml), washed with 20 volumes of PBS and eluted with 2 M NaCl (6×1 ml). Eluted material was precipitated with ethanol, separated by SDS-PAGE (10%) and visualized by western blot (CHAD ab α-80, Larsson et al). The peptide CKFPTKRSKKAGRH (SEQ ID No:7) was diluted in PBS and passed over heparin-sepharose (100 µl), the column was washed with 20 volumes PBS and bound material eluted with 0.5, 1, and 2M NaCl (3 column volumes of each).

Cells and Cell Culture

Human cells (K9) originating from a human chondrosarcoma were a kind gift from Drs. Sven Inerot and Anders Lindahl, The Salgrenska University Hospital Gothenburg, Sweden. The K9 cells were cultured in Dulbeccos Modified Eagle Medium: Nutrient Mixture F12 (DMEM/F12 1:1) with GLUTAMAX I, supplemented with 10% fetal calf serum, 25 µg/ml ascorbic acid, 50 IU of penicillin and 50 µg/ml streptomycin (Life Technologies, Inc.). A different human cells line (K105) originating from a human chondrosarcoma was a kind gift from Dr. Sven Inerot, The Salgrenska University Hospital, Gothenburg, Sweden. The K105 cells were cultured in a mix of 40% Dulbeccos Modified Eagle Medium, 40% Minimum Essential Media (MEM) alpha Medium, 10% Nutrient Mixture F1 supplemented with 100 nM hydrocortisone, 100 ng/ml insulin, 10% fetal calf serum, 25 µg/ml ascorbic acid, 50 IU of penicillin and 50 µg/ml streptomycin (Life Technologies, Inc.). To harvest cells, culture dishes were rinsed three times with $Ca^{2+}/Mg^{2+}$-free PBS and the cells were incubated with 0.5% trypsin and 1 mM EDTA for 5 min. Detached cells were suspended in PBS containing 1 mg/ml trypsin inhibitor (Sigma) and then washed in PBS. To remove membrane-bound collagens the cells were treated with collagenase 100 U/ml (CLSPA; Worthington Biochemical Corp., Lakewood, N.J.) in PBS, 30 min. 37° C. and then washed in PBS.

Bovine chondrocytes were isolated by collagenase (CLS1; Worthington Biochemical Corp., Lakewood, N.J.) digestion of articular cartilage from 4-6 month old calves as described (10). Briefly, cartilage slices were digested for 16 hours with collagenase in EBSS (Earle's balanced salt solution, GIBCO BRL Gaithersburg, Md.). The cells were filtered through a 100 µm nylon filter, washed three times in PBS containing 0.2% BSA (SERVA).

Cell Adhesion

Tissue culture 48-wells dishes (Nunclon, Nunc, Denmark) were coated overnight with 5 µg/ml chondroadherin in 4M Guanidine-HCl, 50 mM sodium acetate, pH 5.8, or for native protein in PBS. Alternatively coating was with 5 µg/ml collagen type II in PBS followed by after-coating with 0.5% BSA in PBS for 3 hours. Collagen type II was isolated from bovine nasal cartilage by pepsin digestion (11). Bacterially expressed chondroadherin was isolated as described above. Recombinant chondroadherin expressed in EBNA cell was cloned and purified as described elsewhere (8).

To test cell binding, the chondrosarcoma cells or bovine chondrocytes were suspended in PBS containing 0.1% BSA, 25 U/ml collagenase and added to the wells (50,000/well), in the absence or presence of various peptide pools or the synthetic peptides (200, 100, 50, 25, 12.5 µg/ml). Non-adherent cells were removed after 1 hour and adhesion was determined by measuring lysosomal N-acetylglucosaminidase (12). Adhesion and spreading was visualized by light microscopy. In the time studies, k105 cells were allowed to adhere for 30 minutes, unbound cells were removed and medium without serum supplemented with or without peptides (250 µg/ml), β1 integrin antibody (clone P4C10, Gibco BRL), EDTA (5 mM) was added. Cell morphology was visualized by light microscopy after 1, 3 and 20 hours.

Coupling of Chondroadherin to Agarose

Recombinant chondroadherin (2.5 mg expressed in EBNA-cells per ml agarose) was coupled to Mini-Leak agarose (Kem En Tec, A/S, Denmark) according to the manufacturer's instructions. The control agarose was treated in the same manner but with no protein added.

Surface Labeling and Membrane Preparation

Human chondrosarcoma cells (k105) suspended in PBS were incubated with EZ-link sulfo NHS-LC biotin (Pierce Chemical Co) at a final concentration of 1 mg/ml for 1 hour at room temperature. The cells were incubated for 10 minutes in 0.1 M glycine in PBS to block free biotin, washed three times in PBS and then resuspended and homogenized in 10 mM KCl, 20 mM Tris/HCl, pH 7.4, 1 mM EDTA (1 ml/$10^6$ cells). Nuclei were removed by centrifugation at 1,500 g for 5 minutes, 0.15 M NaCl was added to the supernatant and the membrane fraction was collected by centrifugation at 50,000 g for 30 minutes. The pellet was suspended in 2 ml 8 M UREA, 2% Triton-X-1000 in TBS pH 7.4 supplemented with COMPLET® protease inhibitor (Roche). The lysate was cleared by centrifugation at 14,000 g for 20 min.

Affinity Purification of Chondroadherin Binding Proteins

The chondroadherin- and controlagarose (1 ml) were packed in mini columns (Bio-Rad, Hercules, Calif.) and equilibrated with 20 volumes running buffer (6M UREA, 1% Triton-X-100 in TBS pH 7.4 supplemented with COMPLET® protease inhibitor (Roche)). Lysate of biotin labeled cells were passed twice over the control-column, incubated overnight with the chondroadherin-agarose with continuous end over end mixing at 4° C. The chondroadherin- and controlagarose were washed with 20 volumes of running buffer and eluted with 0.5 M NaCl, 6 M UREA in TBS pH 7.4 supplemented with COMPLET (1 ml fractions). Eluted proteins were precipitated with ethanol, resuspended and part of the material was digested with heparitinase and chondroitinase ABC at 37° C. overnight. Undigested and digested material was separated by SDS-PAGE 4-12%, electro-transferred to PVDF-membrane (pall), and blocked with 2% BSA in 10 mM Tris/HCl, pH 7.4, 0.15 M NaCl and 2% Tween (blocking buffer). Biotin-labeled proteins were visualized after incubation with streptavidin-HRP (1:5000 in blocking buffer) by chemiluminescence detection using the ECL system (Amersham).

Immunoprecipitation

Biotin-labeled cell surface material was affinity purified on immobilized chondroadherin eluted with 0.5 M NaCl and passed over a desalting-column (PD-10, Pharmacia) equilibrated and eluted with 0.1% triton X-100 in TBS supplemented with COMPLET protease inhibitor. Eluted material was incubated over night with a syndecan-pan-antibody (5 µg/ml, Rapraeger) and the immune complex was collected using prot-A-sepharose. The sepharose was washed 3 times with heparitinase buffer (50 mM Hepes, 50 mM NaOAc, 150 mM NaCl, pH 6.5), resuspended in the same buffer and digested with heparitinase at 37° C. Immunoprecipitated proteins and cell lysate were separated by SDS-PAGE 10% and electro-transferred to PVDF-membrane (pall). The membrane was blocked with 2% BSA in 10 mM Tris/HCl, pH 7.4, 0.15 M NaCl and 2% Tween (blocking buffer). Immunoprecipitated proteins were visualized after incubation with streptavidin-HRP (1:5000 in blocking buffer) by chemiluminescence detection using the ECL system (Amersham). Syndecans expressed by the k105 cells were detected with the syndecan-pan-antibody (1 µg/ml, Rapraeger), anti rabbit HRP (DAKO) antibody and chemiluminescence detection using the ECL system (Amersham) ECL Cell Adhesion, Example II The following experiment is made in order to determine the ability to inhibit cell adhesion.

Study design: Tissue culture dishes (48-wells) were coated with 5 µg/ml chondroadherin expressed in *E. coli* and blocked for non-specific binding with BSA. K 105 cells were suspended in PBS containing 0.1% BSA, 25 U/ml collagenase and added to the wells (50,000/well) in the presence of synthetic peptide to be tested and allowed to adhere for 1 hour at 37° C. Nonadherent cells were removed by washing, and adhesion was determined by analyzing lysosomal hexosaminidase.

Cartilage Explants

The following experiments measure the effect of a peptide on NO release in IL-1 stimulated cartilage.

Study design: A skinned bovine nose (from cows 18-24 months old) was collected at Hörby slaughter house (Team Ugglarp, Sweden). The septum inside the nose was cut out and the mucosa and the perichondrium was removed before the cartilage was placed in PBS with PEST (100 IU penicillin, 100 µg/ml streptomycin) and 2.5 µg/ml Fungizone (all from Invitrogen, Sweden) for 2 hours at room temperature.

Two mm pieces were punched out of the cartilage. Each piece was placed in a 24-well cell culture plate (Falcon, Sweden) containing 1 ml cell culture medium, HAMs F12 (Invitrogen, Sweden) supplemented with 10 µg/ml BSA, 25 mg/ml ascorbate (both from Sigma, Sweden), PEST (100 IU penicillin, 100 mg/ml streptomycin) and 2.5 µg/ml Fungizone. After 24 hours, the medium was changed and the cartilage pieces were stimulated with human recombinant IL-1a, 10 ng/ml (Roche, Sweden). The peptides where tested in triplet at 20 and 400 µM. The cartilage tissue was incubated for another six days, mediums were exchanged every third day. On each occasion the media were collected for measurement of NO (Griess reaction).

Synovial Fibroblasts

The following experiments measure the IL-6 release in IL-1 stimulated synoviocytes.

Study design: From rats with antigen induced arthritis, the hyperproliferative synovium, pannus, was taken from the inflamed knee day four after disease onset. The pannus tissue was cut to small pieces in PBS with PEST (100 IU penicillin, 100 µg/ml streptomycin) and Fungizone (2.5 µg/ml)(all from InVitrogen, Sweden), before incubation in collagenase (400 U/ml, Worthington, USA) for 3 hours at 37° C., 5% $CO_2$. Cells were centrifuged (8 min., room temperature, 1100 rpm.) and suspended in RPMI 1640 supplemented with 10% FCS (InVitrogen, Sweden), PEST and Fungizone and seeded in a 25 $cm^2$ flask at 37° C., 5% $CO_2$. The following day, cells were rinsed once with medium and further incubated. When confluent, cells were trypsinated for 1 min (0.25% Trypsin with EDTA, InVitrogen, Sweden) counted and seeded in 96 well plates, 10000 cells/well/200 µl.

After 24 hours, the medium was changed and the cells were stimulated with human recombinant IL-1a, 50 ng/ml (Roche, Sweden). The peptide to be investigated was tested in triplets in the concentration interval 50-400 µM. After 72 hour incubation at 37° C., 5% $CO_2$, the medium was collected for measurement of NO (Griess reaction) and IL-6 was analyzed by an ELISA, according to the manufacturer's instructions (BD Biosciences, USA).

In vivo antigen induced arthritis.

The following model experiment measure the effect of the investigated compound on knee-joint swelling using antigen induced arthritis.

The effect of locally administered test compound, 400 mM given twice daily, on the development of arthritis in m-BSA antigen induced monoarthritis in rat was evaluated. Animals treated with saline or Methotrexate (in clinically relevant dose) were used as controls.

Study design: Female Dark Agouti rats, weighing approximately 150 g (B&K breeding center, Denmark) were used. The animals were sensitised intradermally at the tail root with 1 mg mBSA (Sigma A-1009) dissolved in 50 mg saline and emulsified in 50 ml Freund's complete adjuvant (Sigma F 5881). Ten days later the rats were shaved (left knee) and challenged with an intraarticular (i.a) injection of 50 mg mBSA dissolved in 50 ml saline. Test compounds were administered intra-articular (left knee) in 50 ml saline four hours before challenge and thereafter twice daily. The development of arthritis (knee diameters) was registered with an odimeter/calliper. The procedures were carried out under a brief Enflurane anaesthesia. The animals were sacrificed at day 4 after challenge/first treatment.

Results

Synthetic Peptides

The candidate peptides were synthesized and purified with reversed phase chromatography by Schafer-N, Denmark. The most preferred peptide sequences are listed in Table 1, wherein cyclisation is indicated by brackets [and], H— N-terminal, and —OH indicates C-terminal, i.e. unprotected amino acid terminal.

TABLE 1

List of preferred peptide sequences.

| SEQ ID No: | No. of amino acids | Linear (L) Cyclic (C) | SEQUENCE |
|---|---|---|---|
| 1 | 5 | L | H-WLEAK-OH (SEQ ID No. 1) |
| 2 | 8 | L | H-LRRWLEAK-OH (SEQ ID No. 2) |
| 3 | 12 | L | H-QLRGLRRWLEAK-OH (SEQ ID No. 3) |
| 4 | 5 | L | H-KRSKK-OH (SEQ ID No. 4) |
| 5 | 6 | L | H-KKAGRH-H (SEQ ID No. 5) |
| 6 | 13 | L | H-KFPTKRSKKAGRH-OH (SEQ ID No. 6) |
| 7 | 14 | L | H-CKFPTKRSKKAGRH-OH (SEQ ID No. 7) |
| 8 | 338 | L | Chondroadherin (SEQ ID No. 8) (see Sequence Listing) |
| 9 | 21 | C | H-[CQLRGLRRWLEAKASRPDATC]-OH (SEQ ID No. 9) |
| 10 | 52 | L | H-SLETLALTNNPWKCTCQLRGLRRWLEAKAS-RPDATCASPAKFKGQHIRDTDA-OH (SEQ ID No. 10) |
| 11 | 14 | L | H-QLRGLRRWLEAKAS-OH (SEQ ID No. 11) |
| 12 | 21 | C | Ac-[CQLRGLRRWLEAKASRPDATC]-NH2 (SEQ ID No. 12) |

TABLE 1-continued

List of preferred peptide sequences.

| SEQ ID No: | No. of amino acids | Linear (L) Cyclic (C) | SEQUENCE |
|---|---|---|---|
| 13 | 7 | C | H-[CWLEAKC]-OH (SEQ ID No. 13) |
| 14 | 14 | C | H-[CQLRGLRRWLEAKC]-OH (SEQ ID No. 14) |
| 15 | 14 | L | Ac-CKFPTKRSKKAGRH-NH2 (SEQ ID No. 15) |
| 16 | 7 | C | H-[CKRSKKC]-OH (SEQ ID No. 16) |

FIG. 1. Adhesion of K9 Cells to Selected Matrix Constituents.

48-well tissue culture dishes were coated with 5 μg/ml collagen type II, tissue extracted bovine chondroadherin, human chondroadherin expressed in EBNA cells and human chondroadherin expressed in E. coli and blocked for non-specific binding with BSA. The cells were allowed to adhere for 1 hour at 37° C. Nonadherent cells were removed by washing and adhesion was determined by analyzing lysosomal N-acetylglucosaminidase. Adhesion is expressed in number of cells, 50,000 cells/well were seeded.

As seen in FIG. 1, the cells adhered equally well to the various substrates. Notably, the native chondroadherin expressed by the EBNA cells showed binding virtually identical to that of the bacterially expressed most likely unfolded protein since coating was done under denaturing conditions of 4M guanidine-HCl and there are no disulphide bonds as the cysteine residues were blocked by N-ethylmaleimide. Therefore binding is most likely mediated by a linear sequence.

Figure 2:
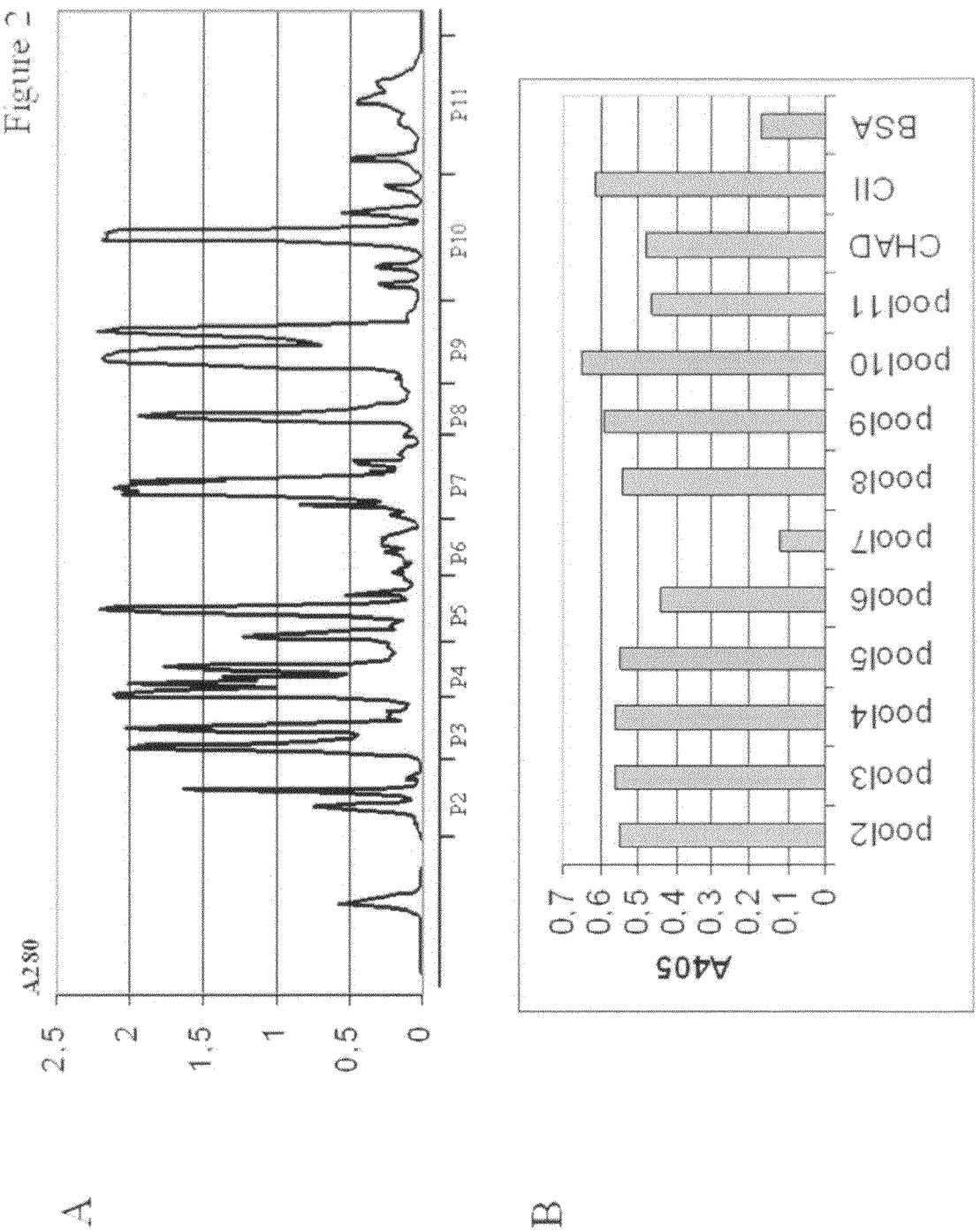
FIG. 2A shows pooling of Sephasil column fractions.
FIG. 2B shows blocking of adhesion of K9 cells to chondroadherin by peptide pools (p1-p11).

FIG. 2. Isolation of Chondroadherin Fragments and Inhibition of Cell Binding by the Peptide Pools.

Recombinant chondroadherin (1 mg) expressed in EBNA-cell was digested with endoproteinase Lys-C and fractionated on a Sephasil C8 column using the SMART™ system (Pharmacia). The effluent was monitored at 280 nm and fractions were pooled as indicated in FIG. 2A (P1-P11). Peptide pools were lyophilized and dissolved in PBS and used in inhibition experiment. 48-wells tissue culture dishes were coated with 5 μg/ml chondroadherin expressed in E. coli and blocked for non-specific binding with BSA. The cells (50,000 cells/well) were allowed to adhere for 1 hour at 37° in the presence of the peptide pools P1-P11 (see FIG. 2B). Nonadherent cells were removed by washing, and adhesion was determined by analyzing lysosomal N-acetylglucosaminidase. Adhesion to collagen type II was used as a positive control and adhesion to BSA coated wells as a negative control. The inhibitory effect of the peptide pools was determined and it was found that P7 was most potent in inhibiting cell adhesion to chondroadherin.

Identification of Protein Fragments in P7

MALDI-TOF MS was used to identify and determine the molecular masses of the chondroadherin fragments in P7. The identified peptides are listed below in Table 2.

TABLE 2

Chondroadherin fragments from P7

| Mass | Amino acid sequence |
|---|---|
| 1029.63 | IPKVSEKTK (SEQ ID No. 25) |
| 1355.72 | FSDGAFLGVTTLK (SEQ ID No. 26) |

TABLE 2-continued

Chondroadherin fragments from P7

| Mass | Amino acid sequence |
|---|---|
| 1775.05 | LRVVEELKLSHNPLK (SEQ ID No. 27) |
| 1947.01 | CTCQLRGLRRWLEAK (SEQ ID No. 28) |

By comparing which peptides were present in fractions of a Glu-C digested recombinant chondroadherin (data not shown), the peptide 1947.01 was selected as the optimal candidate for cell binding.

Figure 3:
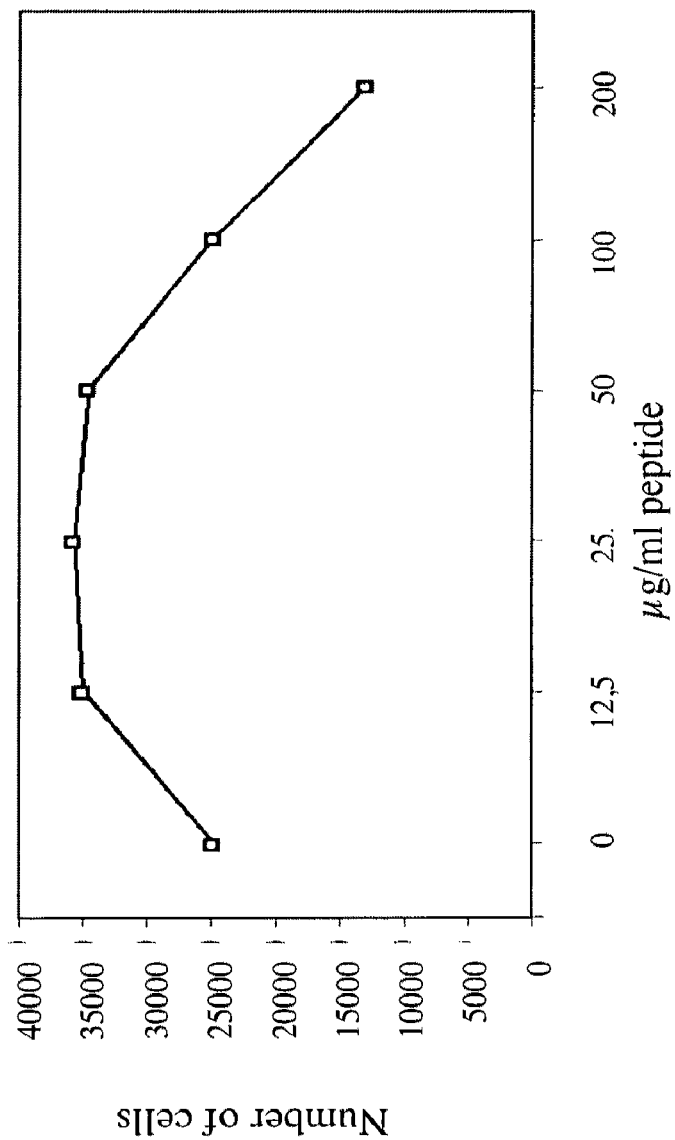
FIG. 3 shows adhesion of k105 cells to chondroadherin.

FIG. 3. Adhesion of K105 Cells to Chondroadherin, Inhibition with the Peptide CQLRGLRRWLEAK (SEQ ID NO. 3).

A 12-mer peptide (1947.01) plus an N-terminal cysteine (CQLRGLRRWLEAK) (SEQ ID NO. 3) representing the candidate sequence identified by mass spectrometry were synthesized and its ability to inhibit cell adhesion was determined. Tissue culture dishes were coated with 5 μg/ml chondroadherin expressed in E. coli and blocked for non-specific binding with BSA. The cells were suspended in PBS containing 0.1% BSA, 25 U/ml collagenase and added to the wells (50,000/well) in the presence of synthetic peptide (200, 100, 50, 25, 12.5 μg/ml) and allowed to adhere for 1 hour at 37° C. Nonadherent cells were removed by washing, and adhesion was determined by analyzing lysosomal hexosaminidase.

Adhesion is expressed as number of cells where the data represent the average of two wells. Independent experiment showed similar results. FIG. 3 shows that adhesion of k105 cells to chondroadherin decreased in a dose dependent manner in the presence of increasing amounts of the 12-mer peptide. This peptide therefore contains a cell binding sequence.

Figure 4:
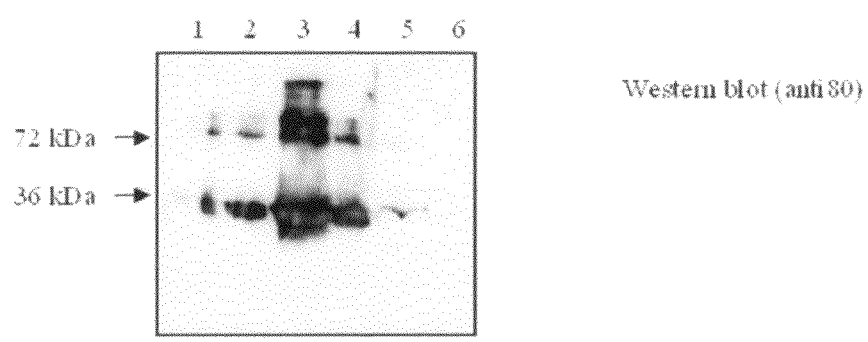
FIG. 4 shows a Western Blot of chondroadherin binding to heparin-sepharose.

FIG. 4. Chondroadherin Heparin-Binding and Identification of a Heparin-Binding Peptide.

Recombinant chondroadherin (10 or 100 μg) expressed in EBNA-cells was passed over Heparin-Sepharose-column (Pharmacia). The column was washed and eluted with 2M NaCl in PBS. Eluted material was separated on SDS-PAGE (10%) and detected by western blot using a chondroadherin antibody (see FIG. 4). The band at 36 kDa represents chondroadherin ant the band at 72 kDa represents a dimer of chondroadherin. It was found that chondroadherin indeed bind to the heparin-sepharose.

The candidate peptide CKFPTKRSKKAGRH (SEQ ID No: 7) was synthesized. The ability of the peptide to bind heparin was confirmed on heparin-sepharose, where material eluted with 0.5, 1 and 2M NaCl was identified by MALDI-TOF MS (data not shown).

FIGS. 5A-5D. Adhesion of K105 Cells to Human Chondroadherin with or without Addition of Two Cell Binding Peptides Interacting with Different Surface Structures.

Figure 5A:
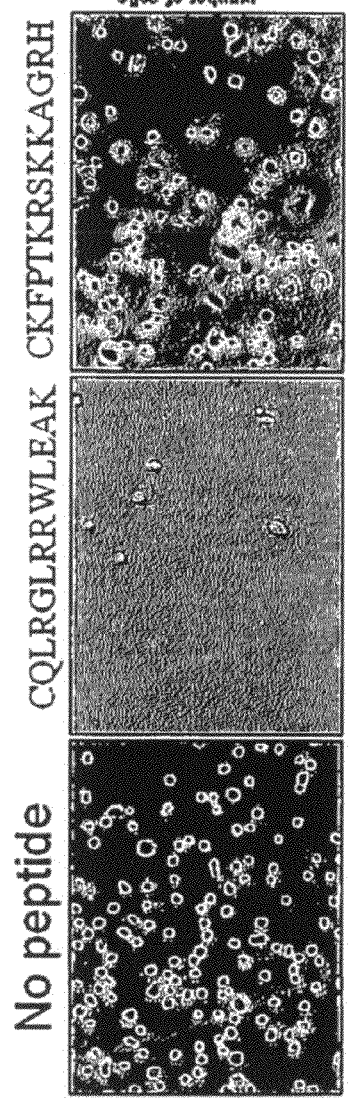
FIGS. 5A-5D show k105 cell adhesion to chondroadherin and collagen type II in the presence and absence of two cell binding peptides.
Figure 5B:
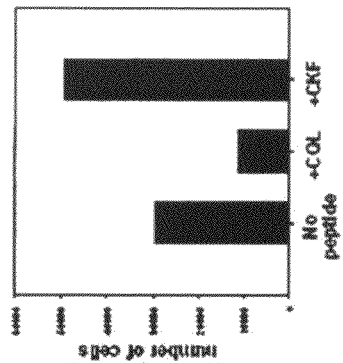
Figure 5C:
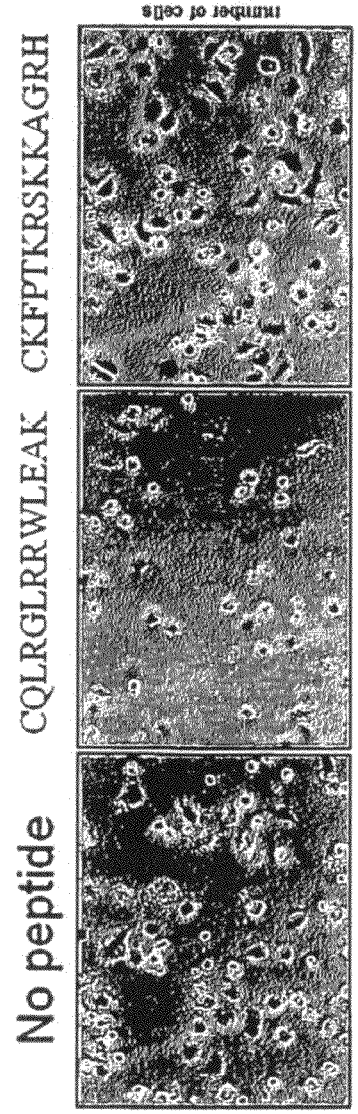
Figure 5D:
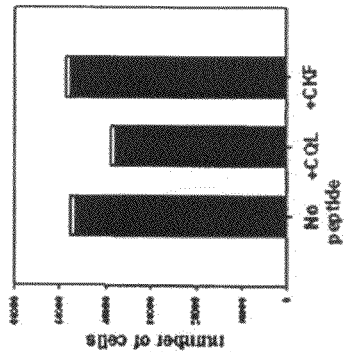

Tissue culture dishes were coated with 5 μg/ml chondroadherin expressed in E. coli or collagen type II and blocked for non-specific binding with BSA. The cells (50,000/well) were suspended in PBS containing 0.1% BSA, 25 U/ml collagenase and added to the wells in the presence or absence of synthetic peptides (250 μg/ml), allowed to adhere for 1 hour at 37° C. Nonadherent cells were removed by washing. Spreading was visualized by light microscopy, and adhesion was determined by analyzing lysosomal hexosaminidase. Adhesion is expressed as number of cells where the data represent the average of two wells. Independent experiment showed similar results. As shown in FIGS. 5A-5D, cell (k105)

adhesion to chondroadherin decreased in the presence of 250 μg/ml of the 12-mer peptide (CQLRGLRRWLEAK) (SEQ ID NO. 3), FIGS. 5A-5B while the adhesion and spreading increased in the presence of 250 μg/ml of the 13-mer heparin binding peptide (CKFPTKRSKKAGRH, SEQ ID No:7). Adhesion to collagen type II (FIGS. 5C-5D) was not significantly affected by any of the two peptides. The data clearly demonstrate two specific cell-binding domains in chondroadherin. One is represented by the heparin binding peptide and one by the apparent integrin binding peptide.

Figure 6:
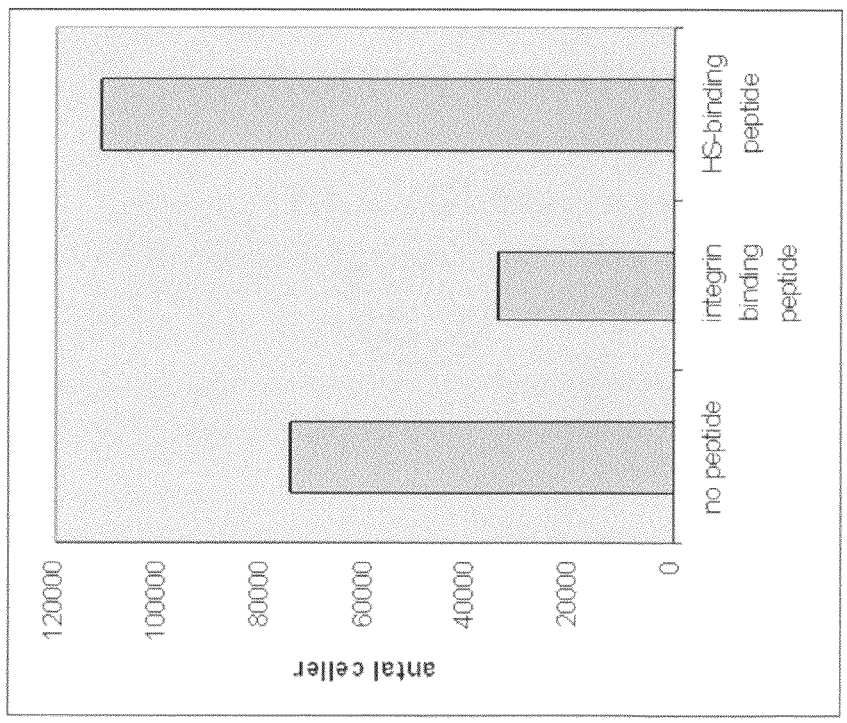
FIG. 6 shows adhesion of bovine chondrocytes to chondroadherin in the presence or absence of cell binding peptides.

FIG. 6. Adhesion of Bovine Chondrocytes to Human Chondroadherin with or Without Addition of Cell Binding Peptides.

Tissue culture dishes were coated with 5 μg/ml chondroadherin expressed in *E. coli* or collagen type II and blocked for non-specific binding with BSA. The bovine chondrocytes (100,000/well) were suspended in PBS containing 0.1% BSA, 25 U/ml collagenase and added to the wells in the presence or absence of synthetic peptide (250 μg/ml) and allowed to adhere for 1 hour at 37° C. Nonadherent cells were removed by washing. Adhesion was determined by analyzing lysosomal hexosaminidase. Adhesion is expressed as number of cells, 100,000 cells/well was seeded. As FIG. 6 shows, bovine chondrocyte adhesion to chondroadherin decreased in the presence of the 12-mer peptide (CQLRGLRRWLEAK) (SEQ ID NO. 3) while the adhesion increased in the presence of the 13-mer heparin binding peptide (CKFPTKRSKKAGRH, SEQ ID No:7). The binding of this peptide to its cell surface molecule will induce signals that increase activity of the cell surface receptor.

Figure 7:
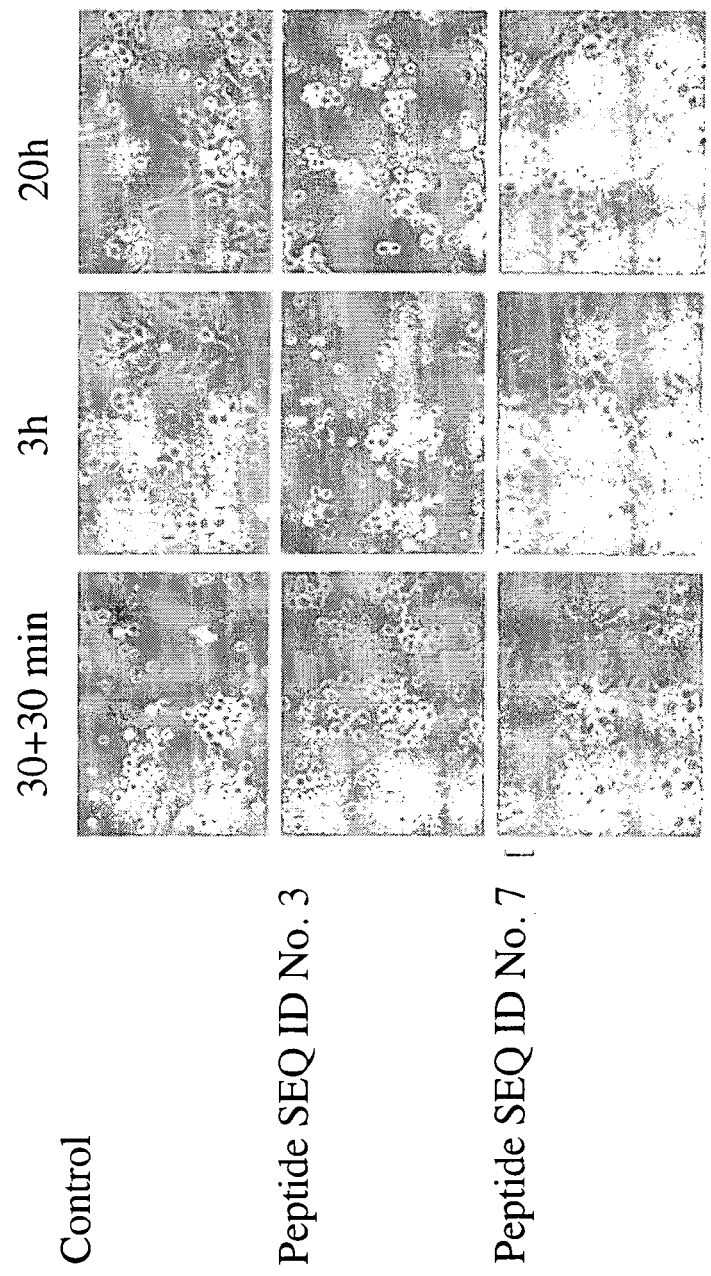
FIG. 7 shows adhesion of k105 cells to chondroadherin with time in the presence or absence of cell binding peptides.

FIG. 7. Adhesion of K105 Cells to Chondroadherin, Effect of Cell Binding Peptides On Adherent Cells.

Tissue culture dishes were coated with 5 μg/ml chondroadherin expressed in *E. coli* and blocked for non-specific binding with BSA. The k105 cells were suspended in PBS containing 0.1% BSA, and added to the wells (50,000/well). Nonadherent cells were removed after 30 min by washing, plain medium without serum with or without peptides (250 μg/ml) was added and bound cells were visualized by light microscopy after 1, 3 and 20 hours. FIG. 7 shows, that the 12-mer peptide (CQLRGLRRWLEAK) (SEQ ID NO. 3) stimulated the cells to form aggregate while spreading and migration increased in the presence of the 13-mer heparin binding peptide (CKFPTKRSKKAGRH, SEQ ID No:7).

FIG. 8. Adhesion of K105 Cells to the Cell Binding Peptides.

Tissue culture dishes were coated with 33 μg/ml (20 □M) peptide solution. The cells (50,000/well) were suspended in PBS containing 0.1% BSA, 25 U/ml collagenase and added to the wells in the presence or absence of synthetic peptide (250 μg/ml) and allowed to adhere for 1 hour at 37° C. Nonadherent cells were removed by washing. Spreading was visualized by light microscopy.

FIG. 8 shows that cells plated on peptide CQLRGLRRWLEAK (SEQ ID NO. 3) adhere and remain round and the adhesion was inhibited in the presence of the same peptide in the solution. Cells plated on peptide CKFPTKRSKKAGRH, SEQ ID No:7, adhere and spread but this peptide was unable to inhibit adhesion at the concentrations tested. It thus appears that the binding to the heparan sulfate binding peptide is considerably tighter or that the cell behavior changes upon binding to this peptide.

Figure 9:
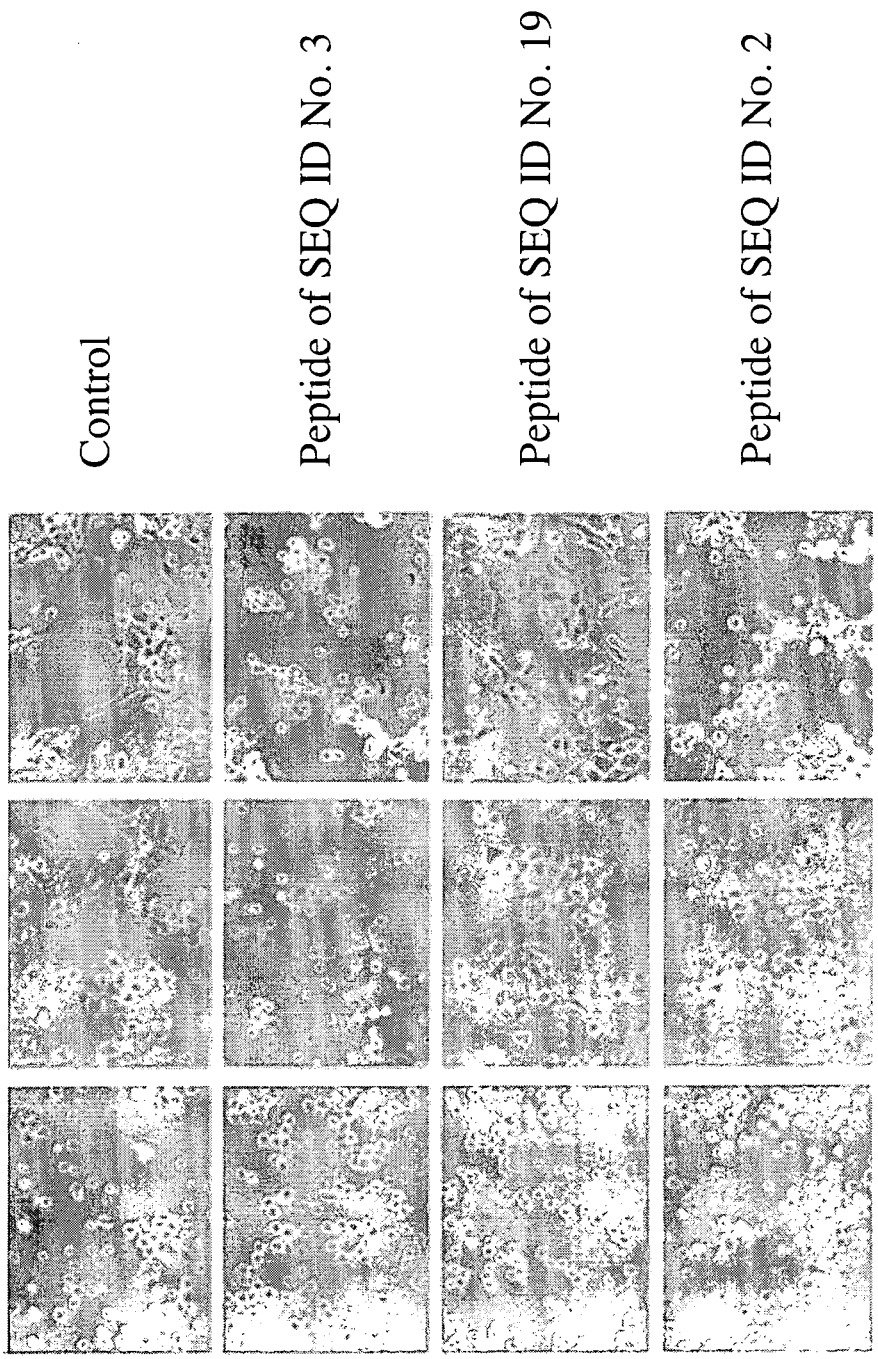
FIG. 9 shows adhesion of k105 cells to chondroadherin with time in the presence of three peptides.

FIG. 9. Adhesion of K105 Cells to Chondroadherin, Determination of a Shorter Sequence of Critical Amino Acids in the Inhibiting Peptide.

Tissue culture dishes were coated with 5 μg/ml chondroadherin expressed in *E. coli* and blocked for non-specific binding with BSA. The cells were suspended in PBS containing 0.1% BSA, and added to the wells (50,000/well). Nonadherent cells were removed after 30 min by washing, plain medium without serum with or without peptides (250 μg/ml) was added and bound cells were visualized by light microscopy after 1, 3 and 20 hours. As seen in FIG. 9, the peptides QLRGLRRWLEAK (SEQ ID 3) and LRRWLEAK (SEQ ID No:2) similarly prevented spreading and induced cells to form aggregates while the peptide QLRGLRRW (SEQ ID No.19) had no effect on cell spreading and migration. The activity for integrin binding is located in the C-terminal eight residues of the sequence involving the WLEAK (SEQ ID No. 1) sequence.

Figure 10:
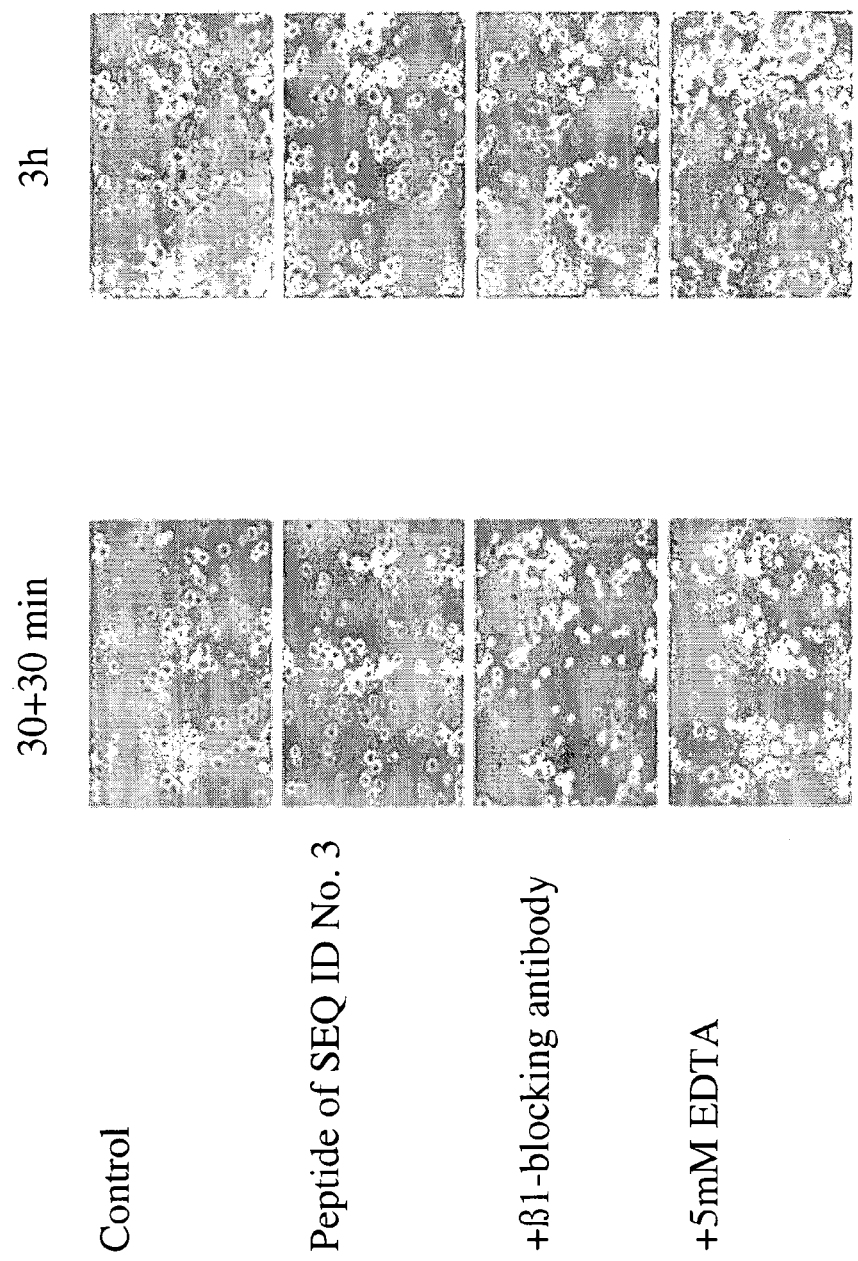
FIG. 10 shows adhesion of k105 cells to chondroadherin and the effect of β integrin antibody and EDTA.

FIG. 10. Adhesion of K105 Cells to Chondroadherin, Effect of β1 Integrin Antibody and EDTA on Adherent Cells Tissue culture dishes were coated with 5 μg/ml chondroadherin expressed in *E. coli* and blocked for non-specific binding with BSA. The k105 cells were suspended in PBS containing 0.1% BSA, and added to the wells (50,000/well). Nonadherent cells were removed after 30 min by washing, peptide, anti β1 antibody, 5 mM EDTA or plain medium without serum was added and bound cells were visualized by light microscopy after 1 and 3 hours. FIG. 10 shows, that the peptide CQLRGLRRWLEAK (SEQ ID NO. 3) and anti β1 antibody prevented spreading and the cells formed aggregate while addition of EDTA lead to cells detaching.

Figure 11:
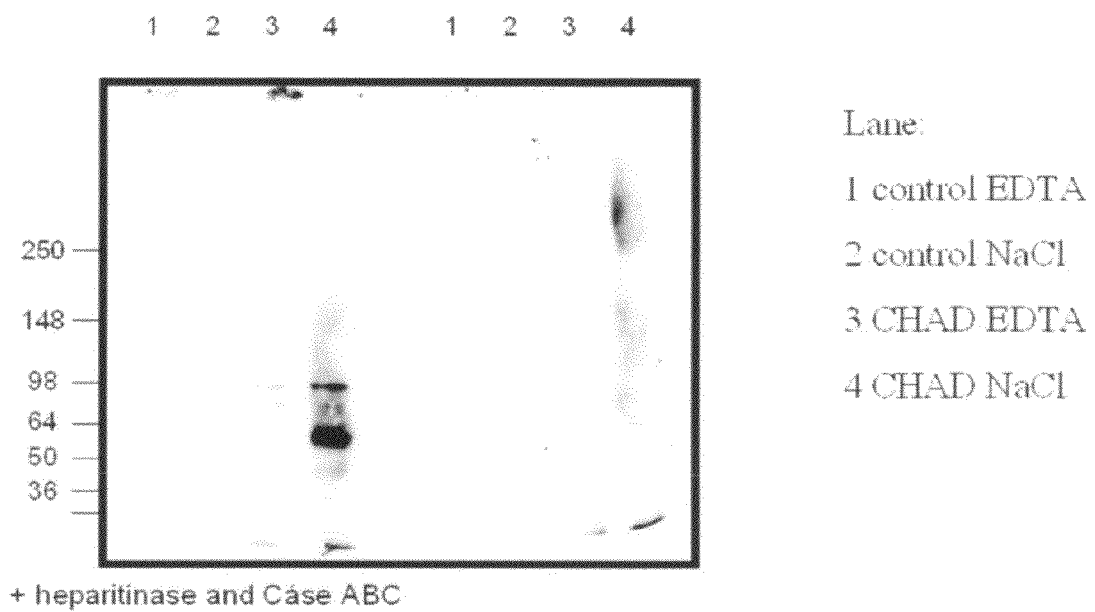
FIG. 11 shows chondroadherin binding membrane proteoglycans on k105 cells.

FIG. 11. Chondroadherin Binding Membrane Proteoglycans on K105 Cells.

Cell surface proteins on human chondrosarcoma cells (K105) were biotin labeled and affinity purified on chondroadherin-agarose in urea. Bound material was eluted with 0.5 M NaCl, separated on SDS-PAGE (4-12%) and detected by Western blot before or after heparitinase and chondroitinase ABC treatment. In separate experiment similar results were obtained by digestion with heparitinase only (see FIG. 11). The component migrating to a position corresponding to some 50-60 kDa after enzyme digestion corresponds to a heparan sulfate proteoglycan found above the 250 kDa marker without enzyme treatment.

Figure 12:
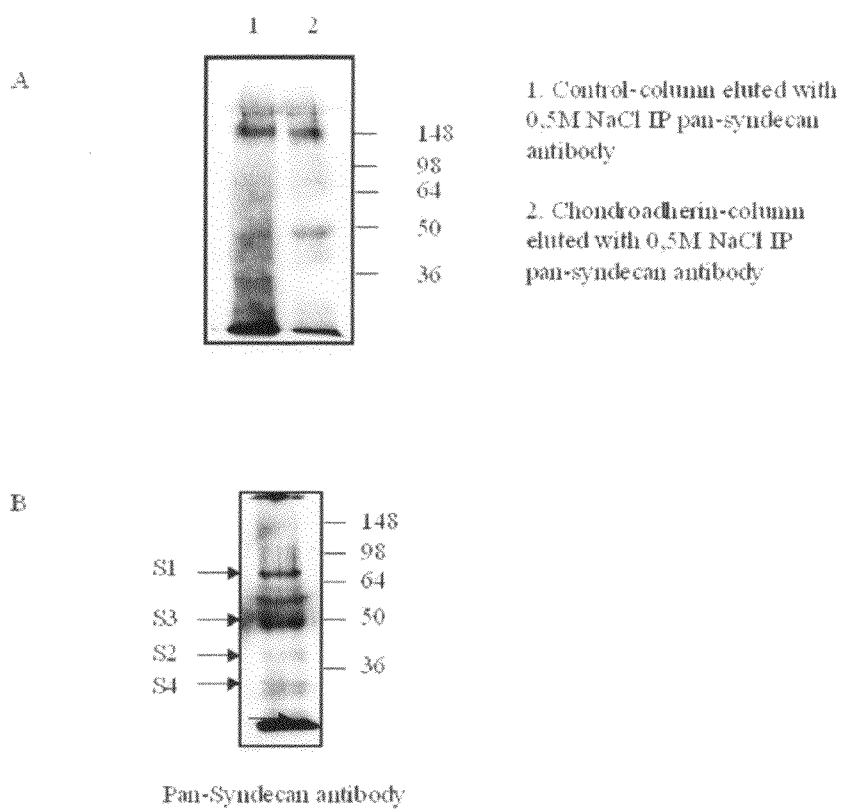
FIG. 12 shows immunoprecipitation of chondroadherin binding proteins with a pansyndecan antibody.

FIG. 12. Immunoprecipitation of Chondroadherin Binding Proteins with a Pan-Syndecan Antibody.

Human chondrosarcoma cells (K105) were surface labeled with biotin and the membranes were extracted with detergent and affinity purified on immobilized chondroadherin. Bound material was eluted with 0.5 M NaCl and immunoprecipitated with a syndecan-pan-antibody, separated by SDS-PAGE (10%) and detected by western blot using streptavidin HRP and the ECL system. As FIG. 12A shows, the antibody immunoprecipitated a protein of about 50 kDa (after heparitinase) from material eluted of the chondroadherin-column whereas no distinct protein band was detected from the control-column (see FIG. 12B).

Syndecans expressed by the K105 cells were detected (after heparitinase) using the syndecan-pan-antibody (see FIG. 12B). Membrane proteins were separated by SDS-PAGE (10%), transferred to a PVDF membrane, incubated with the pan-antibody and detected using an anti rabbit HRP antibody and the ECL system. K105 cells were shown to express Syndecans 1, 2, 3 and 4. The component bound to chondroadherin represents Syndecan 3.

Figure 13:
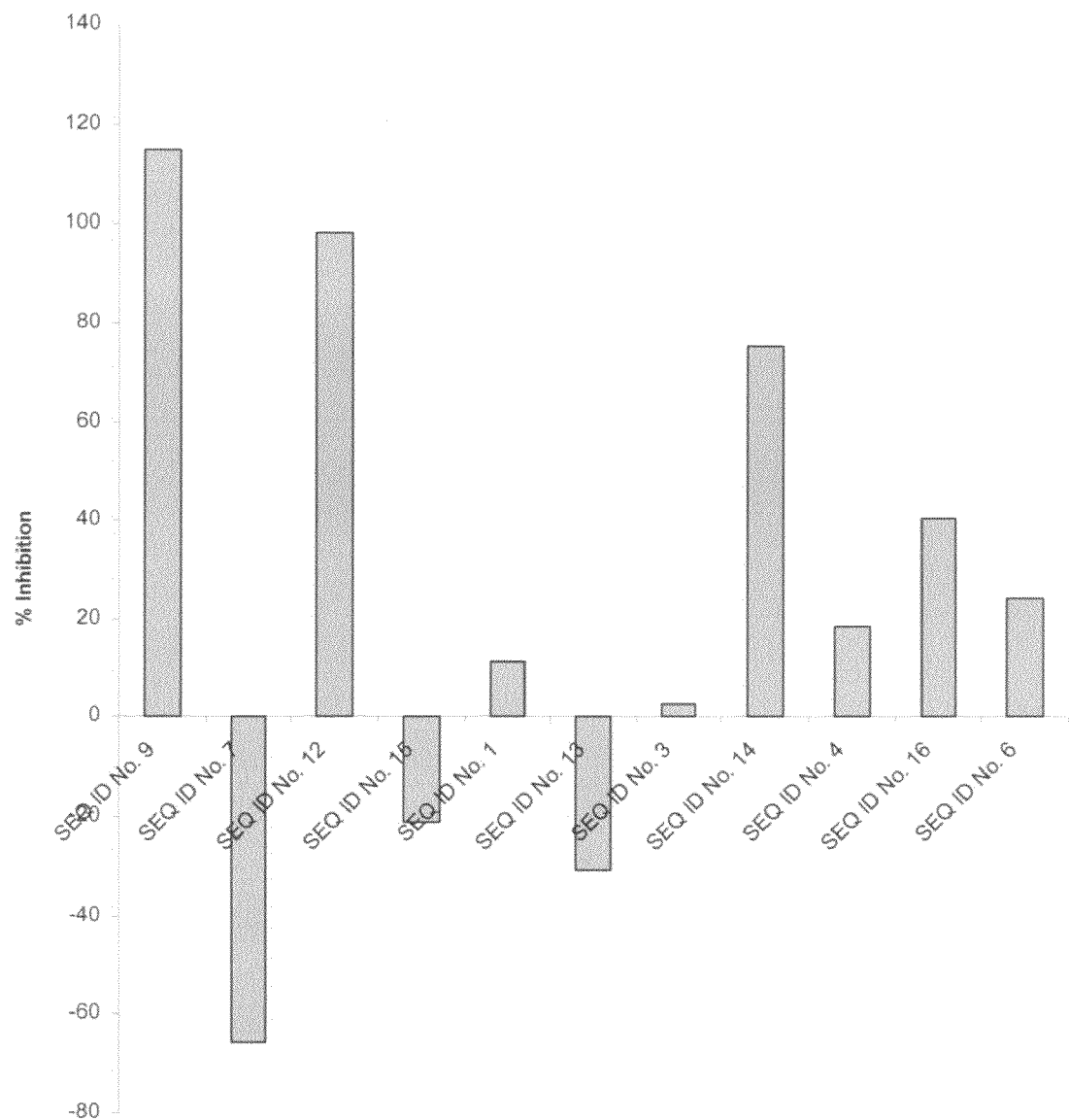
FIG. 13 shows the effect of various peptides on inhibition of cell adhesion.

FIG. 13. Testing of Inhibiting Cell Adhesion, Example II.

The figure shows that the cyclic peptide, H-[CQLRGLRWLEAKASRPDATC]—OH (SEQ ID No:9), and the corresponding protected peptide Ac—[CQLRGLRRWLEAKASRPDATC]-NH2 (SEQ ID No: 12), show inhibitory effect on cell adhesion.

Figure 14:
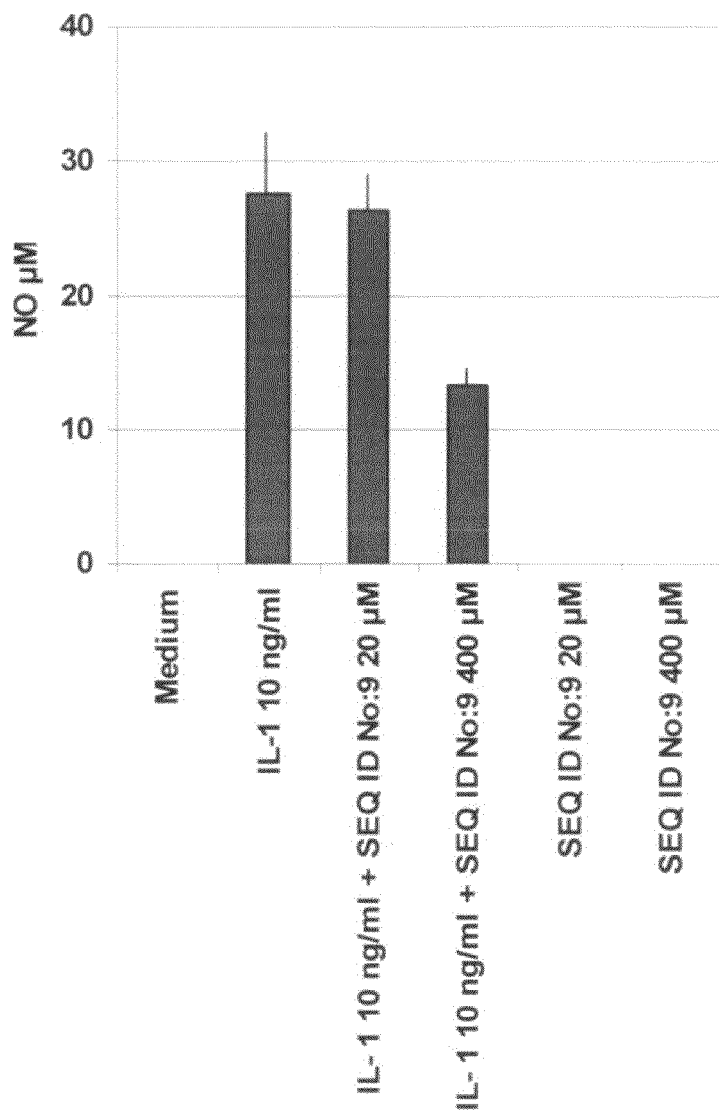
FIG. 14 shows the release of NO from IL-1 stimulated synoviocytes.

FIG. 14. Cartilage Explants Testing.

SEQ ID 9 at a concentration of 400 uM was able to decrease the NO-release from the IL-1 stimulated cartilage explants.

Figure 15:
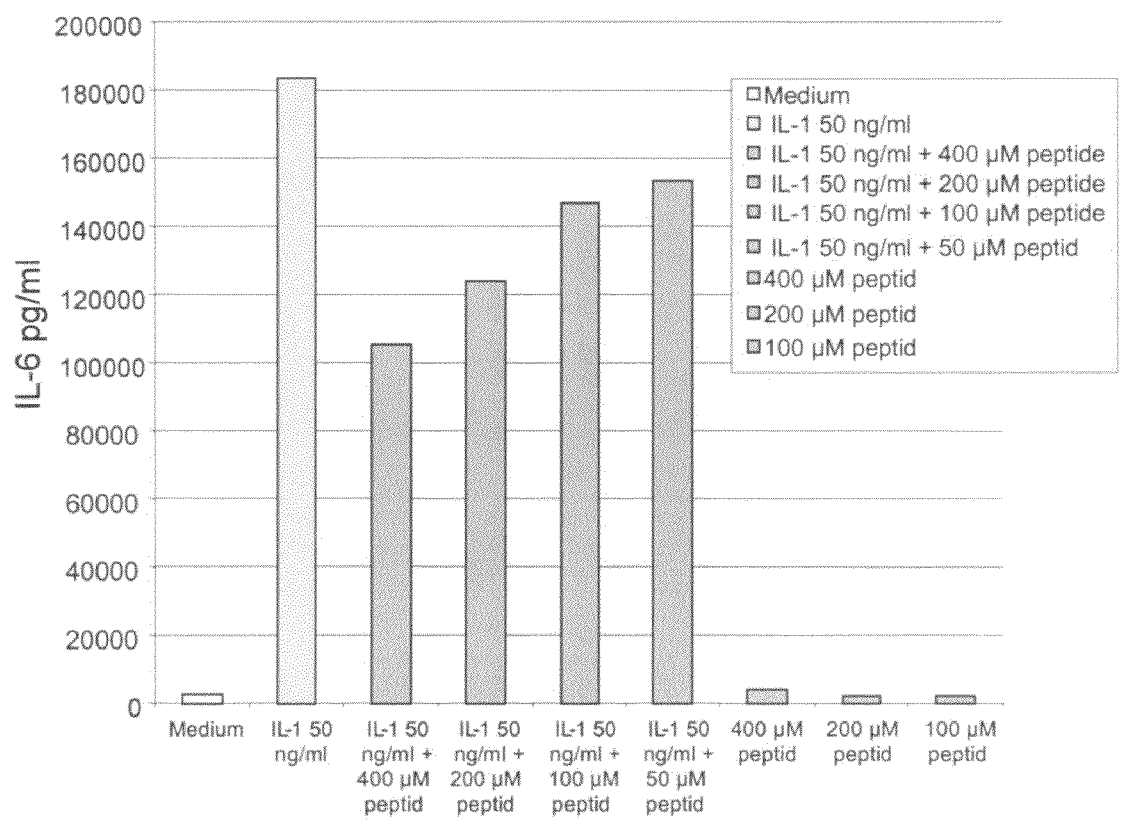
FIG. 15 shows IL-6 release from IL-1 stimulated synoviocytes.

FIG. 15. Synovial Fibroblasts and IL-6 Release.

SEQ ID 9 was able to decrease IL-6-release from IL-1 stimulated synoviocytes in a dose-dependent manner.

Figure 16:
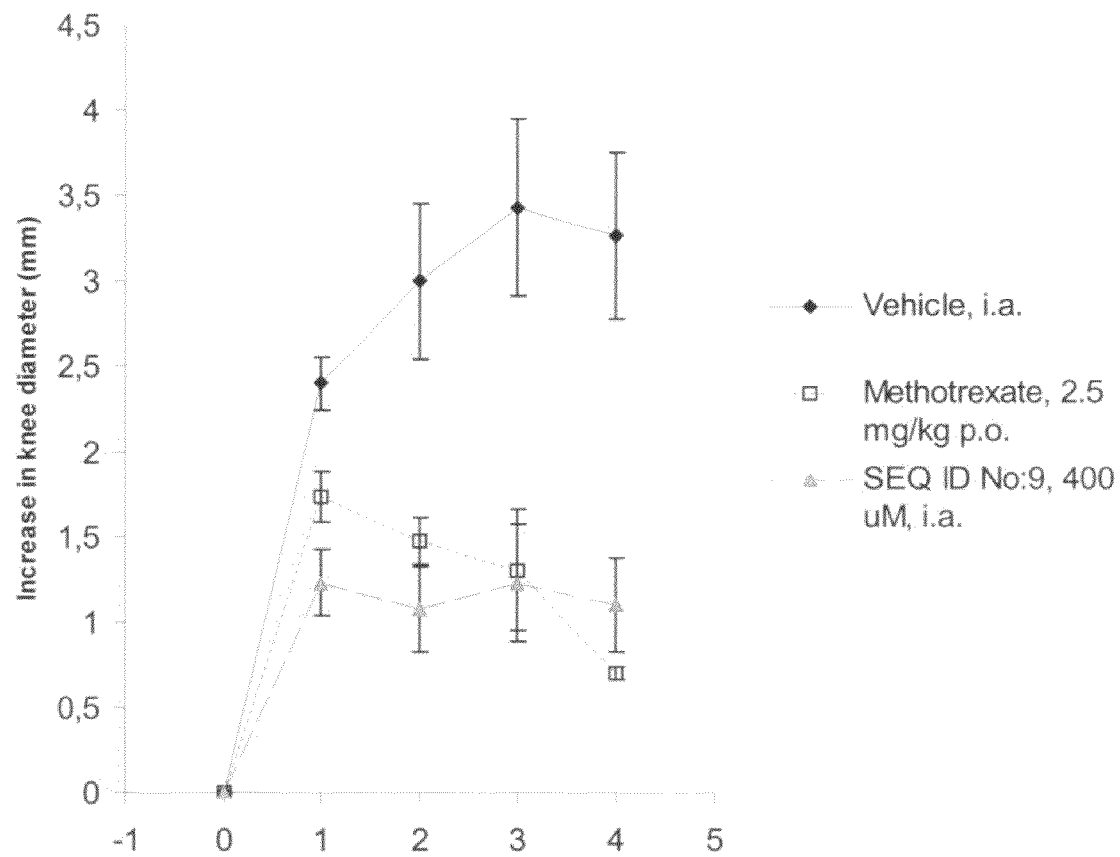
FIG. 16 shows the effect of administration of SEQ ID No:9 on knee-joint swelling.

FIG. 16. In Vivo Antigen Induced Arthritis.

Locally administered peptide SEQ ID 9 decreased the knee-joint swelling compared with saline treated animals. The disease-ameliorating effect was in the same magnitude as methotrexate treatment.

Discussion

Integrin-Binding Fragment from Chondroadherin

A chondroadherin peptide (CQLRGLRRWLEAK) (SEQ ID NO. 3) able to inhibit cell adhesion to the intact protein in a dose dependent manner is identified. Cell adhesion to chondroadherin is mediated via the integrin α2β1 where the adhesion appears to be mediated though its I-domain (9).

In pilot experiments aimed at identifying whether binding might be mediated via a linear sequence, it was shown that human chondrosarcoma cells (K9) adhere equally well to native as to unfolded chondroadherin. This provided strong evidence that a linear peptide sequence mediates binding, facilitating the search for the structure. The use of bacterially expressed chondroadherin lacking substituents provided further support for the notion that binding is mediated via a peptide sequence not involving posttranslational modifications. Knowing that a linear peptide sequence is involved in binding a strategy was devised based on proteolytic cleavage of the EBNA cell expressed protein using two different proteinases to at least in one case retain the active structure. The peptides generated were fractionated and used to inhibit binding of cells to intact protein. Active peptides were identified using MALDITOF mass spectrometry.

Using this protocol, a peptide CQLRGLRRWLEAK (SEQ ID NO. 3) that was shown to inhibit cell (k105) binding in a dose dependent manner was identified. Cells adhering to the peptide CQLRGLRRWLEAK (SEQ ID NO. 3) remain rounded as is observed upon adherence to the intact protein. This 13 residues long peptide should contain a shorter stretch of amino acids still capable of binding to the receptor. To address this question two overlapping peptides, CQLRGLRR (SEQ ID No.21) and LRRWLEAK (SEQ ID No:2) were synthesized. The peptides were added to cells plated on immobilized chondroadherin and it was found that LRRWLEAK (SEQ ID No:2) like CQLRGLRRWLEAK (SEQ ID NO. 3) prevented spreading and induced cells to form aggregate. These results show that the activity for cell binding to be located in the C-terminal eight residues of the sequence involving the WLEAK (SEQ ID No. 1) sequence.

Several reports describe the finding of short peptides with specific activity in blocking the adhesion between one matrix protein and a specific integrin. Many of the peptides are found in the loop structure of disintegrins for example MLD (EC3B and EC6A), VGD (EC3A) (13) and RGD (in several disintegrins) purified from the venom of the viper *E. carinatus*. The α9 and α4 subunits are structurally similar and both recognise VCAM-1 as a ligand. A motif of MLDG found in the disintegrins EC3 and EC6 inhibited α9β1 and α4β1 adhesion to VCAM-1 although concentrations that abolished adhesion of α9 transfected cells to VCAM-1 showed little or no effect on adhesion to the other α9β1 ligands, osteopontin and tenascin-C (13). The peptides SSVYGLR (SEQ ID No.21) and AEIDGIEL (SEQ ID No.22) previously shown to inhibit binding to osteopontin and tenascin-C (14) on the other hand had no effect on α9β1 adhesion to VCAM-1. Another peptide RRETAWA (SEQ ID No.23) compete directly with the α5β1 binding of RGD-containing fibronectin fragments (15). The CPCFLLGCC-peptide (SEQ ID No.24) inhibits β2 adhesion to ICAM-1 and also to von Willebrand factor (16). When immobilized on plastic support β2 integrin leukocyte adhesion but not β1 or β3 integrin-mediated cell adhesion. The LLG sequence exposed on ICAM-1 and von Willebrand factor at sites of vascular injury has been suggested to play a role in binding leukocytes and could possibly be used in a therapeutic approach in inflammatory reactions.

The CHAD interaction with cellular α2β1 has rather specific effects on the cellular phenotype with modulation of matrix protein synthesis (data not shown) and apparent blocked cell division and migration. This phenotype that differs from that induced by collagen II binding should be central in maintaining the chondrocyte role in adult cartilage. This would primarily involve repair and adaptation of the extracellular matrix that is continuously exposed to load that needs to be efficiently dealt with. It is furthermore likely that the activation of the α$_2$β$_1$ integrin has a role in preventing cell death, as indicated by studies of T-lymphocytes (Gendron, S., Couture, J., Aoudjit, F.; Integrin alpha2 beta1 inhibits Fas-mediated apoptosis in T-lymphocytes by protein phosphatase 2A-ependent activation of the MAPK/ERK pathway, J. Biol. Chem. 2003, Sep. 17).

Heparin-Binding Fragment of Chondroadherin Sequence analysis identified clusters of basic amino acids in the very C-terminal part of chondroadherin indicating heparin-binding features. This led to the investigation of whether chondroadherin can bind to heparin. Recombinant chondroadherin was found to bind heparin and the candidate peptide $_{(aa346)}$CKFPTKRSKKAGRH$_{(aa359)}$, SEQ ID No:7, was synthesized and shown to bind heparin. The receptor responsible for the binding was identified to be syndecan 3.

Integrins are the best characterized adhesion receptor family but the syndecans are now recognized as important cell surface adhesion co-receptors that can actively participate in adhesion and signaling (1,2). The peptide $_{(aa346)}$CKFPT-KRSKKAGRH$_{(aa359)}$, SEQ ID No:7, has a profound stimulative effects on cell adhesion, spreading and migration in vitro. Similar effects on cell adhesion have been shown after (PMA) treatment (3, 9, 4, 5). PMA is known to activate protein kinase C signaling and thereby stimulate adhesion and spreading in a process involving syndecan 4 and integrins (3).

Mesenchymal cells use syndecans to adhere to ADAM 12 and β1 integrins to induce spreading (6).

Chondroadherin exist as two forms in the tissue with unknown functional difference where one form lacks the nine last amino acids (Neame P J, Sommarin Y, Boynton R E, Heinegard D., J Biol. Chem. 1994 Aug. 26; 269(34):21547-54.). The heparin binding peptide CKFPTKRSKKAGRH, SEQ ID No: 7, that was synthesized corresponds to this part of chondroadherin.

REFERENCE LIST

1. Couchman, J. R., L. Chen, and A. Woods. 2001. Syndecans and cell adhesion. *Int. Rev. Cytol.* 207:113-150.
2. Rapraeger, A. C. 2000. Syndecan-regulated receptor signaling. *J. Cell Biol.* 149:995-998.
3. Woods, A., R. L. Longley, S. Tumova, and J. R. Couchman. 2000. Syndecan-4 binding to the high affinity heparin-binding domain of fibronectin drives focal adhesion formation in fibroblasts. *Arch. Biochem. Biophys.* 374:66-72.
4. Danilov, Y. N. and R. L. Juliano. 1989. Phorbol ester modulation of integrin-mediated cell adhesion: A post receptor event. *J. Cell Biol.* 108:1925-1933.

5. Wilcox-Adelman, S. A., F. Denhez, and P. F. Goetinck. 2002. Syndecan-4 modulates focal adhesion kinase phosphorylation. *J. Biol. Chem.* 277:32970-32977.
6. Iba, K., R. Albrechtsen, B. Gilpin, C. Frohlich, F. Loechel, A. Zolkiewska, K. Ishiguro, T. Kojima, W. Liu, J. K. Langford, R. D. Sanderson, C. Brakebusch, R. Fassler, and U. M. Wewer. 2000. The cysteine-rich domain of human ADAM 12 supports cell adhesion through syndecans and triggers signaling events that lead to beta1 integrin-dependent cell spreading. *J. Cell Biol.* 149:1143-1156.
8. Mansson, B., Wenglen, C., Morgelin, M., Saxne, T., and Heinegard, D. (2001) *J. Biol. Chem.* 276; 32883-32888
9. Camper, L., Heinegård, D., and Lundgren-Åkerlund, E. (1997) *J. Cell Biol* 138, 1159-1167
10. Sommarin, Y. and Heinegard, D. (1983) *Biochem. J* 214, 777-784
11. Miller, E. J. (1972) *Biochemistry* 11, 4903-4909
12. Landegren, U. (1984) *J. Immunol. Methods* 67, 379-388
13. Sommarin, Y., Larsson, T., and Heinegård, D. (1989) *Exp. Cell Res.* 184, 181-192
14. Barry, S. T., Ludbrook, S. B., Murrison, E., and Horgan, C. M. (2000) *Exp. Cell Res.* 258, 342-351
15. Mould, A. P., Burrows, L., and Humphries, M. J. (1998) *J. Biol. Chem.* 273, 25664-25672
16. Koivunen, E., Ranta, T. M., Annila, A., Taube, S., Uppala, A., Jokinen, M., van Willigen, G., Ihanus, E., and Gahmberg, C. G. (2001) *J. Cell Biol.* 153, 905-916

The invention claimed is:

1. A composition for the treatment of a disease associated with inflammatory mediated cartilage destruction consisting of:

a linear or cyclic compound consisting of the formula 1

P1-X1-X2-X3-X4-X5-X6-X7-X8-W-L-E-A-K-Y1-Y2-Y3-Y4-Y5-Y6-Y7-Y8-P2 wherein
X1 is x is selected from C or absent
X2 is selected from Q or absent
X3 is selected from L or absent
X4 is selected from R, C or absent
X5 is selected from G, K or absent
X6 is selected from L, F or absent
X7 is selected from R, P or absent
X8 is selected from R, C, T or absent
Y1 is selected from A, C or absent
Y2 is selected from S, G or absent
Y3 is selected from R or absent
Y4 is selected from P, H or absent
Y5 is selected from D or absent
Y6 is selected from A or absent
Y7 is selected from T or absent
Y8 is selected from C or absent and P1 and P2 are absent or a protective group,
together with one or more adjuvants, carriers or excipients.

2. A composition for the treatment of a disease associated with inflammatory mediated cartilage destruction consisting of:

a linear or cyclic compound consisting of the formula 1

P1-X1-X2-X3-X4-X5-X6-X7-X8-W-L-E-A-K-Y1-Y2-Y3-Y4-Y5-Y6-Y7-Y8-P2 wherein
X1 is x is selected from C or absent
X2 is selected from Q or absent
X3 is selected from L or absent
X4 is selected from R, C or absent
X5 is selected from G, K or absent
X6 is selected from L, F or absent
X7 is selected from R, P or absent
X8 is selected from R, C, T or absent
Y1 is selected from A, C or absent
Y2 is selected from S, G or absent
Y3 is selected from R or absent
Y4 is selected from P, H or absent
Y5 is selected from D or absent
Y6 is selected from A or absent
Y7 is selected from T or absent
Y8 is selected from C or absent and P1 and P2 are absent or a protective group,
together with one or more adjuvants, carriers or excipients, wherein formula 1 is WLEAK (SEQ. ID No. 1).

3. A composition for the treatment of a disease associated with inflammatory mediated cartilage destruction consisting of:

a linear or cyclic compound consisting of the formula 1

P1-X1-X2-X3-X4-X5-X6-X7-X8-W-L-E-A-K-Y1-Y2-Y3-Y4-Y5-Y6-Y7-Y8-P2 wherein
X1 is x is selected from C or absent
X2 is selected from Q or absent
X3 is selected from L or absent
X4 is selected from R, C or absent
X5 is selected from G, K or absent
X6 is selected from L, F or absent
X7 is selected from R, P or absent
X8 is selected from R, C, T or absent
Y1 is selected from A, C or absent
Y2 is selected from S, G or absent
Y3 is selected from R or absent
Y4 is selected from P, H or absent
Y5 is selected from D or absent
Y6 is selected from A or absent
Y7 is selected from T or absent
Y8 is selected from C or absent and P1 and P2 are absent or a protective group,
together with one or more adjuvants, carriers or excipients wherein formula 1 is LRRWLEAK (SEQ. ID No. 2).

4. A composition for the treatment of a disease associated with inflammatory mediated cartilage destruction consisting of:

a linear or cyclic compound consisting of the formula 1

P1-X1-X2-X3-X4-X5-X6-X7-X8-W-L-E-A-K-Y1-Y2-Y3-Y4-Y5-Y6-Y7-Y8-P2 wherein
X1 is x is selected from C or absent
X2 is selected from Q or absent
X3 is selected from L or absent X4 is selected from R, C or absent
X5 is selected from G, K or absent
X6 is selected from L, F or absent
X7 is selected from R, P or absent
X8 is selected from R, C, T or absent
Y1 is selected from A, C or absent
Y2 is selected from S, G or absent
Y3 is selected from R or absent
Y4 is selected from P, H or absent
Y5 is selected from D or absent
Y6 is selected from A or absent
Y7 is selected from T or absent
Y8 is selected from C or absent and P1 and P2 are absent or a protective group,
together with one or more adjuvants, carriers or excipients wherein formula 1 is CQLRGLRRWLEAK (SEQ. ID No. 3).

5. A composition for the treatment of a disease associated with inflammatory mediated cartilage destruction consisting of:
a linear or cyclic compound consisting of the formula 1

P1-X1-X2-X3-X4-X5-X6-X7-X8-W-L-E-A-K-Y1-Y2-Y3-Y4-Y5-Y6-Y7-Y8-P2 wherein
X1 is x is selected from C or absent
X2 is selected from Q or absent
X3 is selected from L or absent
X4 is selected from R, C or absent
X5 is selected from G, K or absent
X6 is selected from L, F or absent
X7 is selected from R, P or absent
X8 is selected from R, C, T or absent
Y1 is selected from A, C or absent
Y2 is selected from S, G or absent
Y3 is selected from R or absent
Y4 is selected from P, H or absent
Y5 is selected from D or absent
Y6 is selected from A or absent
Y7 is selected from T or absent
Y8 is selected from C or absent and P1 and P2 are absent or a protective group,
together with one or more adjuvants, carriers or excipients wherein formula 1 is H-[CQLRGLRRWLEAKASRP-DATC]-OH (SEQ. ID No. 9).

6. A composition for the treatment of a disease associated with inflammatory mediated cartilage destruction consisting of:
a linear or cyclic compound consisting of the formula 1

P1-X1-X2-X3-X4-X5-X6-X7-X8-W-L-E-A-K-Y1-Y2-Y3-Y4-Y5-Y6-Y7-Y8-P2 wherein
X1 is x is selected from C or absent
X2 is selected from Q or absent
X3 is selected from L or absent
X4 is selected from R, C or absent
X5 is selected from G, K or absent
X6 is selected from L, F or absent
X7 is selected from R, P or absent
X8 is selected from R, C, T or absent
Y1 is selected from A, C or absent
Y2 is selected from S, G or absent
Y3 is selected from R or absent
Y4 is selected from P, H or absent
Y5 is selected from D or absent
Y6 is selected from A or absent
Y7 is selected from T or absent
Y8 is selected from C or absent and P1 and P2 are absent or a protective group,
together with one or more adjuvants, carriers or excipients wherein formula 1 is QLRGLRRWLEAKAS (SEQ. ID No. 11).

7. A composition for the treatment of a disease associated with inflammatory mediated cartilage destruction consisting of:
a linear or cyclic compound consisting of the formula 1

P1-X1-X2-X3-X4-X5-X6-X7-X8-W-L-E-A-K-Y1-Y2-Y3-Y4-Y5-Y6-Y7-Y8-P2 wherein
X1 is x is selected from C or absent
X2 is selected from Q or absent
X3 is selected from L or absent
X4 is selected from R, C or absent
X5 is selected from G, K or absent
X6 is selected from L, F or absent
X7 is selected from R, P or absent
X8 is selected from R, C, T or absent
Y1 is selected from A, C or absent
Y2 is selected from S, G or absent
Y3 is selected from R or absent
Y4 is selected from P, H or absent
Y5 is selected from D or absent
Y6 is selected from A or absent
Y7 is selected from T or absent
Y8 is selected from C or absent and P1 and P2 are absent or a protective group,
together with one or more adjuvants, carriers or excipients wherein formula 1 is Ac-[CQLRGLRRWLEAKASRP-DATC]-NH2 (SEQ. ID No.12).

8. A composition for the treatment of a disease associated with inflammatory mediated cartilage destruction consisting of:
a linear or cyclic compound consisting of the formula 1

P1-X1-X2-X3-X4-X5-X6-X7-X8-W-L-E-A-K-Y1-Y2-Y3-Y4-Y5-Y6-Y7-Y8-P2 wherein
X1 is x is selected from C or absent
X2 is selected from Q or absent
X3 is selected from L or absent
X4 is selected from R, C or absent
X5 is selected from G, K or absent
X6 is selected from L, F or absent
X7 is selected from R, P or absent
X8 is selected from R, C, T or absent
Y1 is selected from A, C or absent
Y2 is selected from S, G or absent
Y3 is selected from R or absent
Y4 is selected from P, H or absent
Y5 is selected from D or absent
Y6 is selected from A or absent
Y7 is selected from T or absent
Y8 is selected from C or absent and P1 and P2 are absent or a protective group,
together with one or more adjuvants, carriers or excipients wherein formula 1 is CWLEAKC (SEQ. ID No.13).

9. A composition for the treatment of a disease associated with inflammatory mediated cartilage destruction consisting of:
a linear or cyclic compound consisting of the formula 1

P1-X1-X2-X3-X4-X5-X6-X7-X8-W-L-E-A-K-Y1-Y2-Y3-Y4-Y5-Y6-Y7-Y8-P2 wherein
X1 is x is selected from C or absent
X2 is selected from Q or absent
X3 is selected from L or absent
X4 is selected from R, C or absent
X5 is selected from G, K or absent
X6 is selected from L, F or absent
X7 is selected from R, P or absent
X8 is selected from R, C, T or absent
Y1 is selected from A, C or absent
Y2 is selected from S, G or absent
Y3 is selected from R or absent
Y4 is selected from P, H or absent
Y5 is selected from D or absent
Y6 is selected from A or absent
Y7 is selected from T or absent
Y8 is selected from C or absent and P1 and P2 are absent or a protective group,
together with one or more adjuvants, carriers or excipients wherein formula 1 is CQL